(12) United States Patent
Amicucci et al.

(10) Patent No.: US 11,066,684 B2
(45) Date of Patent: Jul. 20, 2021

(54) PRODUCTION OF BIOACTIVE OLIGOSACCHARIDES

(71) Applicant: The Regents of the University of California, Oakland, CA (US)

(72) Inventors: Matthew J. Amicucci, Davis, CA (US); Dayoung Park, Brighton, MA (US); Ace Gita Galermo, Greenfield, CA (US); David A. Mills, Davis, CA (US); John Bruce German, Davis, CA (US); Carlito B. Lebrilla, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/012,530

(22) Filed: Jun. 19, 2018

(65) Prior Publication Data

US 2018/0363016 A1    Dec. 20, 2018

Related U.S. Application Data

(60) Provisional application No. 62/522,604, filed on Jun. 20, 2017.

(51) Int. Cl.
| | | |
|---|---|---|
| *C12P 19/00* | (2006.01) | |
| *C07H 3/06* | (2006.01) | |
| *C12P 19/04* | (2006.01) | |
| *C07H 1/08* | (2006.01) | |
| *C08B 37/00* | (2006.01) | |
| *C07H 1/00* | (2006.01) | |

(52) U.S. Cl.
CPC ............... *C12P 19/00* (2013.01); *C07H 1/00* (2013.01); *C07H 1/08* (2013.01); *C07H 3/06* (2013.01); *C08B 37/00* (2013.01); *C12P 19/04* (2013.01)

(58) Field of Classification Search
CPC . C12P 19/00; C12P 19/04; C07H 1/08; C07H 1/00; C07H 3/06; C08B 37/00
See application file for complete search history.

(56) References Cited

U.S. PATENT DOCUMENTS

| 4,629,699 A | 12/1986 | Bianchini |
| 4,933,326 A | 6/1990 | Bianchini |
| 5,253,711 A * | 10/1993 | Mondshine ............... C09K 8/52 |
| | | 166/300 |
| 2015/0184212 A1 | 7/2015 | Bule et al. |

FOREIGN PATENT DOCUMENTS

WO    WO 2016/132130 A1    8/2016

OTHER PUBLICATIONS

Guilloux et al., J. Agric. Food Chem., 2009, vol. 57, p. 11308-11313.*
Hoffman et al., Carbohydrate Research, 2005, vol. 340, p. 1826-1840.*
Sun et al., Carbohydrate Polymers, 2000, vol. 42, p. 111-122.*
International Search Report and Written Opinion dated Sep. 7, 2018 from PCT Application No. PCT/US2018/038350.
Soltes, L., et al., "Degradation of High-Molecular-Weight Hyaluronan by Hydrogen Peroxide in the Presence of Cupric Ions," Carbohydrate Research, 341(5) (2006) 639-644.
Vismara, E., et al., "Low-Molecular-Weight Heparin From $Cu^{2+}$ and $Fe^{2+}$ Fenton Type Depolymerisation Processes," Blood Coagulation, Fibrinolysis and Cellular Haemostasis, 103(3) (2010) 613-622.
Vitale, A., et al., "New Insights of the Fenton Reaction Using Glycerol as the Experimental Model, Effect of $O_2$, Inhibition by $Mg^{2+}$, and Oxidation State of Fe," J. Phys. Chem. A, 120(28) (2016) 5435-5445.
Extended European Search Report for EP Appln. 18820526.4 dated Feb. 11, 2021; 6 pages.
Amicucci, M.J. et al.; "A nonenzymatic method for cleaving polysaccharides to yield oligosaccharides for structural analysis"; *Nature Communications*; vol. 11, No. 1; Aug. 7, 2020; 12 pages.
Panagos, C. et al.; "Structural characterization of oligosaccharides obtained by Fenton-type radical depolymerisation of dermatan sulfate"; *Carbohydrate Polymers*; Applied Science Publishers, Ltd., Barking, GB; vol. 87, No. 3; Oct. 14, 2011; pp. 2086-2092.

* cited by examiner

*Primary Examiner* — Kade Ariani
(74) *Attorney, Agent, or Firm* — Kilpatrick Townsend and Stockton LLP

(57) ABSTRACT

Methods of generating oligosaccharides are provided.

24 Claims, 29 Drawing Sheets

PRODUCTION OF BIOACTIVE OLIGOSACCHARIDES

CROSS-REFERENCE TO RELATED PATENT APPLICATIONS

The present application claims benefit of priority to U.S. Provisional Patent Application No. 62/522,604, filed Jun. 20, 2017, which is incorporated by reference for all purposes.

BACKGROUND OF THE INVENTION

Short chains of sugar molecules from 3 to 20 monosaccharides in length, known as oligosaccharides, have been of significant interest due to their bioactivity. This includes their ability to act as prebiotics, modulate the immune system, and block pathogen adhesion in the gut [Hooper, L. V.; Midtvedt, T.; Gordon, J. I., *Annual review of nutrition* 2002, 22 (1), 283-307]. The best example of these oligosaccharides are those produced in human milk [LoCascio, R. G. et al., *Journal of agricultural and food chemistry* 2007, 55 (22), 8914-8919; Marcobal, A. et al., *Journal of agricultural and food chemistry* 2010, 58 (9), 5334; Wang, M. et al., *Journal of pediatric gastroenterology and nutrition* 2015, 60 (6), 825]. These compounds are known to have high specificity in enriching specific bacteria in the nascent gut.

There have been several efforts in harvesting oligosaccharides from plant and animal-based products. Examples of these include the galactooligosaccharides (GOS) [Lamsal, B. P., *Journal of the Science of Food and Agriculture* 2012, 92 (10), 2020-2028] and fructose oligosaccharides (FOS) [Yoshikawa, J. et al., *Biotechnology letters* 2008, 30 (3), 535-539]. These products are currently employed in nutraceutical and pharmaceutical applications.

With the exception of human milk oligosaccharides, short unconjugated oligosaccharide chains are not readily found in nature. Furthermore, the syntheses of these compounds are costly, and the isolation is difficult as the oligosaccharides do not exist in high abundance in most natural products. Polysaccharides, sugar molecules of up to 100,000 monosaccharides in length, are very abundant in nature from plants, bacteria, and yeast, but are too large to possess biological activity.

Fenton's chemistry is based upon generating hydroxyl and hydroperoxyl radicals using an iron catalyst [Neyens, E.; Baeyens, J., *Journal of Hazardous materials* 2003, 98 (1), 33-50; Walling, C., *Accounts of chemical research* 1975, 8 (4), 125-131], these radical products can in turn oxidize a variety of different substrates [Kuo, W., *Water Research* 1992, 26 (7), 881-886; Lin, S. H.; Lo, C. C., *Water research* 1997, 31 (8), 2050-2056; Watts, R. J. et al., *Hazardous Waste and Hazardous Materials* 1990, 7 (4), 335-345; Zazo, J. et al., *Environmental science & technology* 2005, 39 (23), 9295-9302]. Notably, Fenton's oxidation has been used as an analytical tool to determine nucleic acid complexes and protein-protein interactions by the selective scission of their respective polymers [Meares, C. F. et al., *Methods in enzymology* 2003, 371, 82-106; Rana, T. M.; Meares, C. F., *Journal of the American Chemical Society* 1990, 112 (6), 2457-2458]. Oxidation and oxidative degradation of carbohydrates with and without an iron catalyst have been of great interest, especially in functionalizing starch and cellulose and degrading wood polysaccharides [Emery, J. A. et al., *Wood Science and Technology* 1974, 8 (2), 123-137; Xu, G.; Goodell, B., *Journal of Biotechnology* 2001, 87 (1), 43-57; Haskins, J. F.; Hogsed, M. J., *The Journal of Organic Chemistry* 1950, 15 (6), 1264-1274; Šelih, V. S. et al., *Polymer Degradation and Stability* 2007, 92 (8), 1476-1481; Parovuori, P. et al., *Starch-Stärke* 1995, 47 (1), 19-23]. The mechanisms and results of Fenton type oxidations on mono-, di-, and oligosaccharides has been studied by a number of researchers. Fenton's oxidation of carbohydrates tend to have inherent specificity. Disaccharides have been shown to be more readily oxidized than monosaccharides and sugar alcohols [Morelli, R. et al., *Journal of Agricultural and Food Chemistry* 2003, 51 (25), 7418-7425], while (1→6) linkages tend to be more labile than (1→4) linkages [Uchida, K.; Kawakishi, S., *Carbohydrate Research* 1988, 173 (1), 89-99].

More recently, the Fenton systems have been used for the depolymerization of chondroitin sulfate, heparin, and other glycosaminoglycans [Achour, O. et al., *Carbohydrate Polymers* 2013, 97 (2), 684-689; Li, J.-h. et al., *Marine Drugs* 2016, 14 (9), 170; Petit, A. C. et al., *Carbohydrate Polymers* 2006, 64 (4), 597-602; Wu, M. et al., *Carbohydrate Polymers* 2010, 80 (4), 1116-1124]. All these papers use an acid containing substrate in the form of iduronic or glucuronic acid residues.

BRIEF SUMMARY OF THE INVENTION

A method for the formation of oligosaccharide from polysaccharides is provided. In some embodiments, the method comprises reacting polysaccharides with hydrogen peroxide and $Fe^{3-}$, $Fe^{2+}$, $Cu^{2-}$ or other metals as discussed herein followed by cleaving glycosidic linkages in the polysaccharides with a base, thereby generating oligosaccharides from the polysaccharides. This reaction is referred to as "FITDOG" herein.

We developed a method for producing bioactive oligosaccharides by digesting polysaccharides from plants, bacteria, and yeast. The method employs the Fenton reagent composed of iron ($Fe^{3+}$, $Fe^{2+}$) or other transition metal (including but not limited to, $Cu^{1+}$, $Co^{2+}$, etc.) and hydrogen peroxide. In some embodiments, the oligosaccharides are produced in the range of DP 3 to 20 (DP refers to degree of polymerization). In some embodiments, the described method will produce oligosaccharides for analysis and for bioactive foods that are prebiotic, anticancer, pathogen blocking, or have other functions.

The method can be used to convert polysaccharides (e.g., from plants, bacteria, or yeast) into bioactive oligosaccharides. The method involves the reaction of polysaccharides with $Fe^{3+}$ and hydrogen peroxide. Other metal ions that include but are not limited to $Fe^{2+}$ and $Cu^{2+}$ also produce the same results with variable efficacy. In some embodiments, the reaction is allowed to proceed for 30 minutes (or for example, between 10 minutes and 4 hours, e.g., 15 minutes to 2 hours or 10 minutes to one hour). The reaction is subsequently quenched with base (e.g., aqueous sodium hydroxide calcium hydroxide, potassium hydroxide, etc.).

In some embodiments, the resulting oligosaccharides can be characterized. In some embodiments, high performance liquid chromatography-mass spectrometry (LC-MS) analysis of the product mixture shows a number of oligosaccharide structures ranging in size from a degree of polymerization of 3 to as many as 20 (or from 3 to up to 200 for example), depending on the polysaccharide source. The oligosaccharide structures and compositions depend on the polysaccharide sources.

In some embodiments, production of oligosaccharides from plant sources consisting of degrees of polymerization (DP) from 3 to 20 (or from 3 to up to 200 for example) is provided. The polysaccharides can include for example those from known foods such as rice, banana, squash, wheat flour and polysaccharides as byproduct of food production. In some embodiments, the polysaccharides can come from waste food products and from sources not usually considered food. In some embodiments, the source of polysaccharide is processed foods and plant products.

In some embodiments, the method provides for the production of oligosaccharides (e.g., having a degree of polymerization between DP 3 and 20 (or from 3 to up to 200 for example)) from bacterial cell wall polysaccharides.

In some embodiments, the method provides for the production of oligosaccharides (e.g., having a degree of polymerization between DP 3 and 20 (or from 3 to up to 200 for example)) from yeast cell wall polysaccharides.

In some embodiments, the method provides for the production of oligosaccharides (e.g., having a degree of polymerization between DP 3 and 20 (or from 3 to up to 200 for example)) from algae polysaccharides.

In some embodiments, the oligosaccharides are bioactive oligosaccharides. In some embodiments, the bioactive oligosaccharides are consumed by bacteria beneficial to the human gut. In some embodiments, the bioactive oligosaccharides can modulate the immune system. The oligosaccharide can cause the immune system to under or overreact to known and unknown stimuli. In some embodiments, the bioactive oligosaccharides function as a pathogen block.

In some embodiments, the oligosaccharides are selective carbon substrates to stimulate growth of the microbiota of soils. In some embodiments, the oligosaccharides are added to soil following a fumigation or sterilization protocols on the soil. Accessible organic carbon can drive the soil ecology in a pathogenic direction if uncontrolled. By providing specific oligosaccharides that selectively stimulate growth of beneficial soil microbiota, soil pathogen populations in the soil can be reduced. In some embodiments, a combination of one or more oligosaccharide prepared as described herein can be added to soil with one or more microbe (e.g., beneficial soil microbes).

In some embodiments, one or more oligosaccharide prepared as described herein can be used to generate a prebiotic for food supplementation. In some embodiments, the oligosaccharides can contribute to appetite control and/or control of energy (caloric) intake in children with overweight and obesity.

In some embodiments, a method is provided for creating soluble fiber from insoluble fiber comprising polysaccharides using the reaction conditions described herein. By running the reaction only to a certain extent, one can generate compositions have desirable characteristics (e.g., gels or salves). Soluble fiber products can be useful for a number of uses, including but not limited to medical products and devices, food products (i.e. thickeners, nutritional amendments, flavor modifications), soil amendments (to enrich specific beneficial soil microbiome constituents), and fiber production (i.e. novel textiles, ropes, biodegradable packaging etc.). In some embodiments, for example, the insoluble fiber is cotton.

In some embodiments, methods of generating oligosaccharides from polysaccharides are provided. In some embodiments, the method comprises, reacting polysaccharides in a reaction mixture with hydrogen peroxide and a transition metal or an alkaline earth metal; followed by quenching the reaction with a base and/or cleaving glycosidic linkages in the polysaccharides with a base, thereby generating a mixture of oligosaccharides from the polysaccharides. In some embodiments, the reaction mixture comprises a transition metal. In some embodiments, the transition metal is selected from iron (e.g., $Fe^{3+}$, $Fe^{2+}$), copper (e.g., $Cu^{2+}$), manganese, cobalt, or molybdenum. In some embodiments, the reaction mixture comprises an alkaline earth metal. In some embodiments, the alkaline earth metal is selected from calcium or magnesium.

In some embodiments, the transition metal or alkaline earth metal in the reaction mixture is at a concentration of at least 0.65 nM. In some embodiments, the transition metal or alkaline earth metal in the reaction mixture is at a concentration from 0.65 nM to 500 nM. In some embodiments, the hydrogen peroxide in the reaction mixture is at a concentration of at least 0.02 M. In some embodiments, the hydrogen peroxide in the reaction mixture is at a concentration of from 0.02 M to 1 M. In some embodiments, the base is sodium hydroxide, potassium hydroxide or calcium hydroxide. In some embodiments, the base is at a concentration of at least 0.1 M. In some embodiments, the base is at a concentration of from 0.1 M-5.0 M. In some embodiments, the polysaccharides include one or more of amylose, amylopectin, betaglucan, pullulan, xyloglucan, arabinogalactan I and arbinogalactan II, rhamnogalacturonan I, rhamnogalacturonan II, galactan, arabinan, arabinoxylan, xylan (e.g., beechwood xylan), glycogen, mannan, glucomannan, curdlan, or inulin. In some embodiments, the polysaccharides are from a plant or animal source. In some embodiments, the polysaccharides are from a bacterial or algal source. In some embodiments, the polysaccharides are in the form of (optionally lyophilized) plant material. In some embodiments, the plant material is banana, chick pea or millet plant material. In some embodiments, the method further comprises purifying one or more oligosaccharide from the mixture of oligosaccharides.

In some embodiments, prior to the reacting, the method comprises contacting polysaccharides with one or more polysaccharide degrading enzyme. In some embodiments, the one or more polysaccharide degrading enzyme comprises an amylase, isoamylase, cellulase, maltase, glucanase, or a combination thereof.

Also provided are compositions comprising the mixture of oligosaccharides as generated in the method above or elsewhere herein or the purified one or more oligosaccharide as generated in the method above or elsewhere herein.

Also provided is an oligosaccharide of Table 1, or a mixture of two or more oligosaccharide of Table 1.

Also provided is a method of stimulating microbes in vitro or in vivo. In some embodiments, the method comprises contacting a microbe (e.g., bacteria, fungi, yeast) with a composition comprising the mixture of oligosaccharides as generated in the method above or as described elsewhere herein (e.g., Table 1) or an oligosaccharide of Table under conditions to selectively stimulate growth of the microbe. In some embodiments, the microbes are probiotic microbes. In some embodiments, the microbes are in the gut of an animal and the composition is administered to the animal. In some embodiments, the probiotic microbe is administered to the animal, either separately from the composition or simultaneously with the composition. In some embodiments, the probiotic microbe is *Bifidobacterium pseudocatenulatum*. In some embodiments, the microbes are soil microbes, oral microbes (e.g., bacteria), or skin microbes (e.g., bacteria).

Definitions

The "degree of polymerization" or "DP" of an oligosaccharide refers to the total number of sugar monomer units that are part of a particular oligosaccharide. For example, a tetra galacto-oligosaccharide has a DP of 4, having 3 galactose moieties and one glucose moiety.

The term "*Bifidobacterium*" and its synonyms refer to a genus of anaerobic bacteria having beneficial properties for humans. *Bifidobacterium* is one of the major strains of bacteria that make up the gut flora, the bacteria that reside in the gastrointestinal tract and have health benefits for their hosts. See, e.g., Guarner F and Malagelada J R. *Lancet* (2003) 361, 512-519, for a further description of *Bifidobacterium* in the normal gut flora.

A "prebiotic" or "prebiotic nutrient" is generally a non-digestible food ingredient that beneficially affects a host when ingested by selectively stimulating the growth and/or the activity of one or a limited number of microbes in the gastrointestinal tract. As used herein, the term "prebiotic" refers to the above described non-digestible food ingredients in their non-naturally occurring states, e.g., after purification, chemical or enzymatic synthesis as opposed to, for instance, in whole human milk.

A "probiotic" refers to live microorganisms that when administered in adequate amounts confer a health benefit on the host.

As used herein, the terms "about" and "approximately," when used to modify an amount specified in a numeric value or range, indicate that the numeric value as well as reasonable deviations from the value known to the skilled person in the art, for example ±20%, ±10%, or ±5%, are within the intended meaning of the recited value.

DETAILED DESCRIPTION OF THE INVENTION

Figure 1:
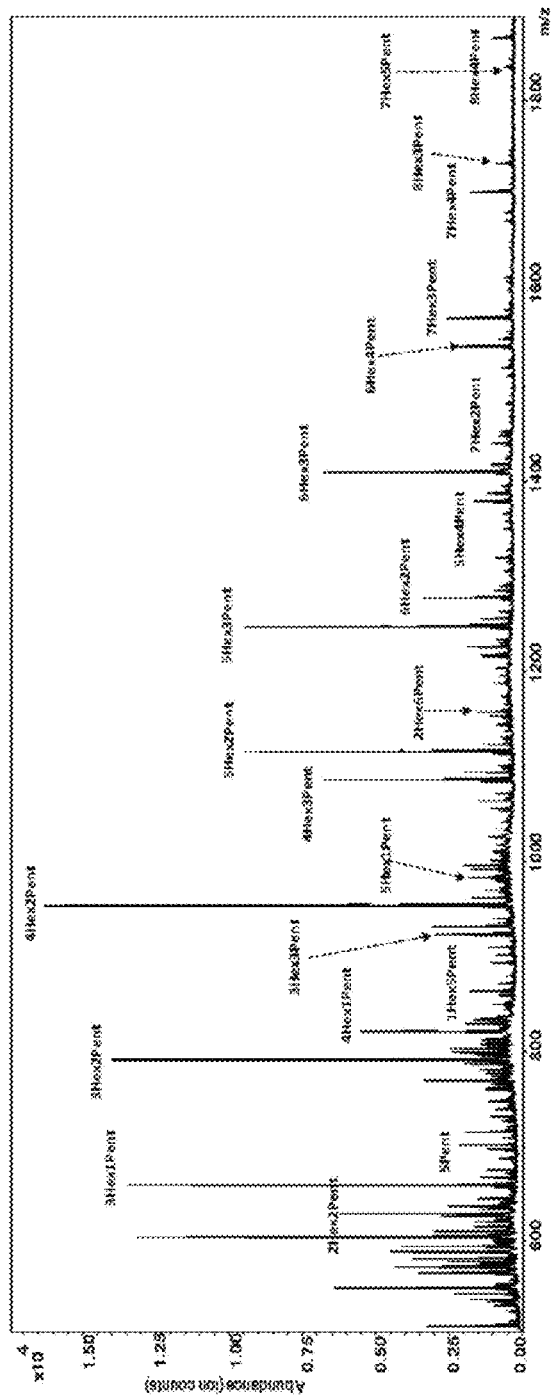
FIG. 1. Example MALDI-MS for xyloglucan oligosaccharides produced by FITDOG.

Fenton's Initiation Toward Defined Oligosaccharide Groups (FITDOG) is a method for the controlled degradation of polysaccharides into oligosaccharides. In some embodiments, the crude polysaccharides first undergo initial oxidative treatment with the hydrogen peroxide and a transition metal or alkaline earth metal (e.g., iron(III) sulfate) catalyst to render the glycosidic linkages more labile. NaOH or other base is then used for base induced cleavage, which results in a variety of oligosaccharides. Immediate neutralization takes place to reduce the peeling reaction. This method has the ability to generate large amounts of biologically active oligosaccharides from a variety of carbohydrate sources.

If desired, the polysaccharide can be optionally treated with one or more polysaccharide-degrading enzyme to reduce the average size or complexity of the polysaccharide before the resulting polysaccharides are treated with the oxidative treatment and metal catalyst. Non-limiting examples of polysaccharide enzymes include for example, amylase, isoamylase, cellulase, maltase, glucanase, or a combination thereof.

The initial oxidative treatment can include hydrogen peroxide and a transition metal or an alkaline earth metal. Metals with different oxidation states, sizes, periodic groups, and coordination numbers have been tested to understand the application with the FITDOG process. Each of the different metals has shown activity in the FITDOG reaction. While these metals work with any polysaccharide, different metals can be used to produce oligosaccharides with preferential degrees of polymerization. The oxidative treatment is followed by a base treatment. The method is capable of generating oligosaccharides from polysaccharides having varying degrees of branching, and having a variety of monosaccharide compositions, including natural and modified polysaccharides. This method will work with polysaccharides from any source. Exemplary polysaccharide substrates include, but are not limited to, one or more of amylose, amylopectin, betaglucan, pullulan, xyloglucan, arabinogalactan I and arbinogalactan II, rhamnogalacturonan I, rhamnogalacturonan II, galactan, arabinan, arabinoxylan, xylan (e.g., beechwood xylan), glycogen, mannan, glucomannan, curdlan, or inulin.

In some embodiments, the resulting mixture of oligosaccharides generated by the method can have on average a degree of polymerization between 2-200, e.g., between 2-100 or 3-20 or 5-50.

The resulting mixture of oligosaccharides generated by the method can have a variety of uses. In some embodiments, the mixture of oligosaccharides can be used as a prebiotic to selectively stimulate growth of one or more probiotic bacteria. In some embodiments, the oligosaccharide compositions can be administered as a prebiotic formulation (i.e., without bacteria) or as a probiotic formulation (i.e., with desirable bacteria such as bifidobacteria as described herein). In general, any food or beverage that can be consumed by humans or animals may be used to make formulations containing the prebiotic and probiotic oligosaccharide containing compositions. Exemplary foods include those with a semi-liquid consistency to allow easy and uniform dispersal of the prebiotic and probiotic compositions described herein. However, other consistencies (e.g., powders, liquids, etc.) can also be used without limitation. Accordingly, such food items include, without limitation, dairy-based products such as cheese, cottage cheese, yogurt, and ice cream. Processed fruits and vegetables, including those targeted for infants/toddlers, such as apple sauce or strained peas and carrots, are also suitable for use in combination with the oligosaccharides of the present invention. Both infant cereals such as rice- or oat-based cereals and adult cereals such as Musilix are also suitable for use in combination with the oligosaccharides. In addition to foods targeted for human consumption, animal feeds may also be supplemented with the prebiotic and probiotic oligosaccharide containing compositions.

Alternatively, the prebiotic and probiotic oligosaccharide containing compositions can be used to supplement a beverage. Examples of such beverages include, without limitation, infant formula, follow-on formula, toddler's beverage, milk, fermented milk, fruit juice, fruit-based drinks, and sports drinks. Many infant and toddler formulas are known in the art and are commercially available, including, for example, Carnation Good Start (Nestle Nutrition Division; Glendale, Calif.) and Nutrish A/B produced by Mayfield Dairy Farms (Athens, Tenn.). Other examples of infant or baby formula include those disclosed in U.S. Pat. No. 5,902,617. Other beneficial formulations of the compositions include the supplementation of animal milks, such as cow's milk.

Alternatively, the prebiotic and probiotic oligosaccharide containing compositions can be formulated into pills or tablets or encapsulated in capsules, such as gelatin capsules. Tablet forms can optionally include, for example, one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge or candy forms can comprise the compositions in a flavor, e.g., sucrose, as well as pastilles comprising the compositions in an inert base, such as gelatin and glycerin or sucrose and acacia emulsions, gels, and the like containing, in addition to the active ingredient, carriers known in the art. The prebiotic or probiotic oligosaccharide containing formulations may also contain conventional food supplement fillers and extenders such as, for example, rice flour.

In some embodiments, the prebiotic or probiotic oligosaccharide containing composition will further comprise a non-human protein, non-human lipid, non-human carbohydrate, or other non-human component. For example, in some embodiments, the compositions comprise a bovine (or other non-human) milk protein, a soy protein, a rice protein, betalactoglobulin, whey, soybean oil or starch.

The dosages of the prebiotic and probiotic oligosaccharide containing compositions will be varied depending upon the requirements of the individual and will take into account factors such as age (infant versus adult), weight, and reasons for loss of beneficial gut bacteria (e.g., antibiotic therapy, chemotherapy, disease, or age). The amount administered to an individual, in the context of the present disclosure should be sufficient to establish colonization of the gut with beneficial bacteria over time. The size of the dose also will be determined by the existence, nature, and extent of any adverse side-effects that may accompany the administration of a prebiotic or probiotic oligosaccharide containing composition. In some embodiments, the dosage range will be effective as a food supplement and for reestablishing beneficial bacteria in the intestinal tract. In some embodiments, the dosage of an oligosaccharide composition of the present invention ranges from about 1 micrograms/L to about 25 grams/L of oligosaccharides. In some embodiments, the dosage of an oligosaccharide composition is about 100 micrograms/L to about 15 grams/L of oligosaccharides. In some embodiments, the dosage of a oligosaccharide composition is about 1 gram/L to about 10 grams/L of oligosaccharides. Exemplary Bifidobacterium dosages include, but are not limited to, about $10^4$ to about $10^{12}$ colony forming units (CFU) per dose. A further advantageous range is about $10^6$ to about $10^{10}$ CFU.

The prebiotic or probiotic oligosaccharide containing formulations can be administered to any individual in need thereof. In some embodiments, the individual is an infant or toddler. For example, in some embodiments, the individual is less than, e.g., 3 months, 6 months, 9 months, one year, two years or three years old. In some embodiments, the individual is between 3-18 years old. In some embodiments, the individual is an adult (e.g., 18 years or older). In some embodiments, the individual is over 50, 55, 60, 65, 70, or 75 years old. In some embodiments, the individual is immunodeficient (e.g., the individual has AIDS or is taking chemotherapy).

Exemplary Bifidobacterium that can be included in the probiotic compositions of the invention include, but are not limited to, Bifidobacterium longum subsp. infantis, B. longum subsp. longum, Bifidobacterium breve, Bifidobacterium adolescentis, and B. pseudocatenulatum. The Bifidobacterium used will depend in part on the target consumer.

It will be appreciated that it may be advantageous for some applications to include other Bifidogenic factors in the formulations described herein. Such additional components may include, but are not limited to, fructoligosaccharides such as Raftilose (Rhone-Poulenc, Cranbury, N.J.), inulin (Imperial Holly Corp., Sugar Land, Tex.), and Nutraflora (Golden Technologies, Westminister, Colo.), as well as lactose, xylooligosaccharides, soyoligosaccharides, lactulose/lactitol and galactooligosaccharides among others. In some applications, other beneficial bacteria, such as *Lactobacillus, Rumminococcus, Akkermansia, Bacteroides, Faecalibacterium* can be included in the formulations.

The oligosaccharides as described herein, can be used to stimulate microbes of any sort. Examples of microbes that can be stimulated by the oligosaccharides include, for example, soil microbes (e.g., mycorrhizal fungi and bacteria and other microbes used as soil inoculants such as *Azosprillum* sp.), oral bacterial (e.g., *Streptococcus mutans, Streptococcus gordonii, Streptococcus sanguis*, and *S. oralis*) and skin bacteria (e.g., *Propionibacterium acnes*, also ammonia oxidizing bacteria, including but not limited to *Nitrosomonas, Nitrosococcus, Nitrosospira, Nitrosocvstis, Nitrosolobus*, and *Nitrosovibrio*.

In some embodiments, the oligosaccharide compositions are administered to a human or animal in need thereof. For example, in some embodiments, the oligosaccharide compositions are administered to a person or animal having at least one condition selected from the group consisting of inflammatory bowel syndrome, constipation, diarrhea, colitis, Crohn's disease, colon cancer, functional bowel disorder (FBD), irritable bowel syndrome (IBS), excess sulfate reducing bacteria, inflammatory bowel disease (IBD), and ulcerative colitis. Irritable bowel syndrome (IBS) is characterized by abdominal pain and discomfort, bloating, and altered bowel function, constipation and/or diarrhea. There are three groups of IBS: Constipation predominant IBS (C-IBS), Alternating IBS (A-IBS) and Diarrhea predominant IBS (D-IBS). The oligosaccharide compositions are useful, e.g., for repressing or prolonging the remission periods on Ulcerative patients. The oligosaccharide compositions can be administered to treat or prevent any form of Functional Bowel Disorder (FBD), and in particular Irritable Bowel Syndrome (MS), such as Constipation predominant IBS (C-IBS), Alternating IBS (A-IBS) and Diarrhea predominant IBS (D-IBS); functional constipation and functional diarrhea. FBD is a general term for a range of gastrointestinal disorders which are chronic or semi-chronic and which are associated with bowel pain, disturbed bowel function and social disruption.

In another embodiment, the oligosaccharide compositions are administered to those in need stimulation of the immune system and/or for promotion of resistance to bacterial or yeast infections, e.g., *Candidiasis* or diseases induced by sulfate reducing bacteria.

EXAMPLE

Example 1

The ability to create oligosaccharides from polysaccharides through depolymerization is an attractive solution. Currently polysaccharides are depolymerized in two ways, acid hydrolysis and enzymatic treatment with glycosyl hydrolases. Both techniques have their own drawbacks, acid hydrolysis tends to produce large amounts of monosaccharides and very little amounts of oligosaccharides. On the other hand, enzymatic treatment can produce large amounts of oligosaccharides, but each glycosyl hydrolase can only cleave at very specific sites dependent on the linkage position, stereochemistry, and monosaccharide arrangement of the surrounding environment. This means that even if enzymes capable of depolymerizing a specific polysaccharide are known and available, it would not be capable of large scale degradation of the structurally diverse polysaccharides that occur in natural products.

While there are reports of cellulose and acid containing polysaccharide depolymerization, there is yet to be a method that can effectively depolymerize neutral polysaccharides using Fenton systems. Furthermore, the use of Fenton systems to prepare large amounts of oligosaccharides from crude natural products with high yields has not been shown. The example below aims to show both analytical and preparative scale methods and applications of Fenton's Initiation Towards the Dissociation of Oligosaccharide Groups (FITDOG) for the creation of oligosaccharides in high yield from both polysaccharide isolates and from natural products.

Methods

Materials

Foods were obtained from a local supermarket. Sodium Acetate, hydrogen peroxide (30% w/w), sodium hydroxide, iron(III) sulfate pentahydrate, and glacial acetic acid were all purchased from Sigma-Aldrich (St. Louis, Mo.).

Small Scale Fenton's Initiation Towards the Dissociation of Oligosaccharide Groups (FITDOG))

A solution was prepared containing 95% (v/v) sodium acetate buffer adjusted to pH 5 with glacial acetic acid, 5% (v/v) hydrogen peroxide (30% w/w), and 65 nM iron(III) sulfate. This mixture was vortexed and was added to dry polysaccharide standards to make a final solution of 1 mg/ml. The reaction was incubated at 100° C. for 20 minutes. After reacting, half of the reaction volume of cold 2 M NaOH was added and vortexed before adding 0.6% of the initial reaction volume of concentrated acetic acid to neutralize.

Small Scale FITDOG Generated Oligosaccharide Purification

Oligosaccharides were isolated using nonporous graphitized carbon cartridges (GCC-SPE). Cartridges were washed with 80% acetonitrile in 0.1% (v/v) trifluoroacetic acid (TFA) and nano-pure water. The oligosaccharides were loaded and washed with 5 column volumes of nano-pure water. The oligosaccharides were eluted with 40% acetonitrile with 0.05% (v/v) TFA.

Large Scale Fenton's Initiation Towards the Dissociation of Oligosaccharide Groups (FITDOG)

Food was lyophilized to complete dryness and ground to a fine powder in a KRUPS F203 Grinder (Millville, N.J.). A 950 ml solution of 40 mM sodium acetate buffer adjusted to pH 5 with glacial acetic acid was brought to a boil in a 2 liter round bottom flask equipped with a cold water column condenser. To the flask, 1.0 grams of ground, lyophilized food, 32 mg of iron(III) sulfate, and 50 ml of 30% (w/w) hydrogen peroxide in water is added to the flask. The solution is allowed to react for 20 minutes with a stir bar. To induce cleavage, 500 ml of ice cold 2 M NaOH is added and stirred for 30 seconds before 61.5 ml of ice cold glacial acetic acid is added to neutralize the reaction.

Large Scale FITDOG Generated Oligosaccharide Purification

Flocculated iron was removed by filtering through 0.45 µm polyvinylidene-fluoride (PVDF) filter. A self-packed 50 g porous graphitized carbon (PGC) flash liquid chromatography (Flash-LC) column was used with a CombiFlash Rf200 (Teledyne Isco) flash liquid chromatograph. The sample was loaded onto the column at a rate of 7 ml/min. A binary solvent system was used and consisted of A: nano-pure water and B: acetonitrile (HPLC grade). The sample was washed with 100% solvent A for 20 minutes at 10 ml/min before starting a gradient from 0% to 80% solvent B over 140 minutes, then isocratic at 80% solvent B for 20 minutes. Eluent was directed to waste except from minutes 40-100, where it was collected into a glass bottle. Collected eluent was dried on a rotary evaporator for 1 hour to remove acetonitrile. The remaining liquid was evaporated in a lyophilizer.

Analysis by Matrix Assisted Laser Desorption Ionization Mass Spectrometry (MALDI-MS)

Samples were reconstituted in nano-pure water. 1 µl of samples was plated directly onto a stainless steel MALDI plate. To this 0.3 µl of 0.01M NaCl and 0.7 µl of 25 mg/ml 2,5-dihydroxybenzoic acid were added and mixed within the pipet tip. The samples were then dried under vacuum. Samples were ran on a Bruker UltraFlextreme MALDI-TOF/TOF instrument. The instrument was operated in positive mode and used 95% of max laser power.

Analysis by Chip-HPLC-Nano/Quadrapole Time-of-Flight Mass Spectrometry (Chip-HPLC-Nano/Q-TOF MS)

Samples were reconstituted in nano-pure water before analysis by chip-HPLC-nano/Q-TOF MS. The system includes two pumps, a capillary pump for sample loading and a nano pump for analytical separation. In this system an Agilent 1200 series HPLC is coupled to an Agilent 6520 Q-TOF mass spectrometer through a chip cube interface. The chip contains a 40 nl enrichment column and a 75 µm×43 mm analytical column, both columns are packed with PGC. Sample loading was done with 3% (v/v) acetonitrile/water+0.1% formic acid at a flow rate of 4 µl/min. Chromatographic separation was performed with a binary gradient of solvent A: (3% (v/v) acetonitrile/water+0.1 formic acid) and solvent B: (90% acetonitrile/water+0.1% formic acid) with a flow rate of 0.4 µl/min. The gradient was run for 60 minutes, 1% B to 5% B in 2 min, then 5% to 30% in 33 min, then 30% to 99% over 5 min, then held at 99% for 10 min, then from 99% to 1% in 1 min, then held at 1% for 9 min before starting the next run.

Data were collected in the positive mode and calibrated with internal calibrant ions ranging from m/z 118.086 to 2721.895. Drying gas was set to 325° C. and with a flowrate of 5 l/min. the fragment, skimmer, and Octapole 1 RF voltages were set to 175, 60, and 750 volts, respectively. Fragmentation was performed at a rate of 0.63 spectra/second. The collision energy was based upon the compound mass and expressed as (Collision Energy)=1.8*(m/z)−2.4.

Monosaccharide Composition

Dried butternut squash and FITDOG oligosaccharides underwent monosaccharide composition as follows. Briefly, 10 mg of sample was reconstituted into 138 µl of nano-pure water. Samples were solubilized by adding approximately 100 mg of 1.4 mm stainless steel beads and beat blasting for two minutes in a Next Advance Storm 24 Bullet Blender (Averill Park, N.Y.) and cooked for 1 hour at 100° C. Next, 68 µl of concentrated TFA was added, making a 4 M solution, and incubated for 2 hours at 100° C. To quench, 800 µl of ice cold nano-pure water was added, and the solution was diluted 1000 fold. 50 µl of the diluted solution was dried under vacuum. The dried samples were then derivatized with 3-methyl-1-phenyl-2-pyrazoline-5-one and dried. Samples were then reconstituted in nano-pure water and extracted twice with chloroform, the aqueous layer was used for analysis. Samples were injected into an Agilent 1290 Infinity II UHPLC coupled with an Agilent 6495 QqQ MS. Separation occurred on an Agilent Zorbax Eclipse Plus C18 column (2.1 mm×150 mm i.d., 1.8 µm particle size). The solvent system consisted of A: 25 mM ammonium acetate adjusted to pH 8.2 using $NH_4OH$ in 5% acetonitrile/$H_2O$. All other instrument parameters followed.

Bacterial Consumption

Several bacterial species, mostly *Bifidobacterium* strains, were screened for their ability to metabolize FITDOG oligosaccharides pools. To complete this objective, pure cultures harvested at late exponential phase were used to inoculate basal MRS containing the following different carbon sources: 2% Glucose (positive control), 2% and 5% w/v of Butternut squash oligosaccharides (BSL) and no carbon source (negative control). Cultures were incubated at 37 C in anaerobic conditions for 96 hours, and growth was monitored every 30 minutes using a Biotek plate reader Model EON 120928C (Biotek Instruments Inc, Winooski, Vt., USA). Growth monitoring was done by measuring absorbance at 600 nm after 30 seconds of shaking.

Results

Optimization of FITDOG Reaction Conditions

The Fenton reaction was optimized under various conditions using a commercial xyloglucan (polysaccharide) standard. Concentrations of iron(III) sulfate and hydrogen peroxide, reaction time, temperature, reaction pH, and quenching NaOH concentrations were sequentially optimized using the analytical scale FITDOG procedure. MALDI-TOF MS was used to monitor the oligosaccharide products. MS abundances were used directly to obtain relative oligosaccharide concentrations. The MALDI TOF-MS spectra (FIG. 1) was used to obtain the relative abundances of the respective products.

1. Optimization of $Fe_2(SO_4)_3$ Concentration

Figure 2:
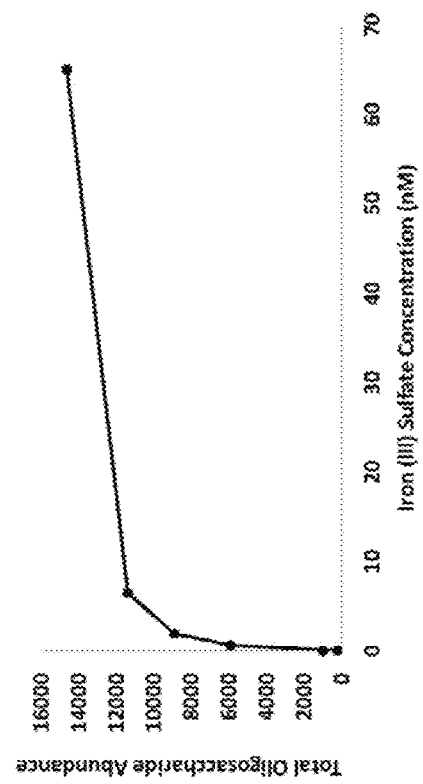
FIG. 2. Optimization of Iron(III)sulfate concentrations to yield optimal oligosaccharide abundances.

Iron(III) sulfate was optimized by varying the concentrations from 0.0065 nM to 65 nM. No oligosaccharide abundances were observed with less than 0.65 nM. The total OS abundances increased with concentration as shown in FIG. 2. At approximately 10 nM $Fe_2(SO_4)_3$ concentration, the signal reached maximum and increased slightly at 65 nM. For this reason, the latter concentration was used for the preparation.

2. Optimization of Buffer pH

Figure 3:
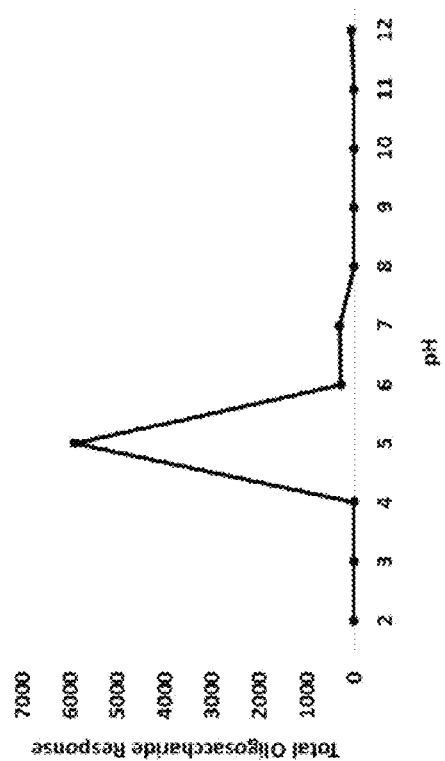
FIG. 3. Optimization of Buffer pH to yield optimal oligosaccharide abundances.

The pH condition was optimized using a sodium acetate buffer and adding appropriate amounts of acid and base (acetic acid and NaOH (aq)) corresponding to pH between 2 and 12 in increments of 1 pH unit. The pH less than 5 did not produce observable amounts. The pH 5 yielded the greatest abundances of oligosaccharides, while beyond 6 also yielded very little abundances (FIG. 3). We therefore chose a pH of 5 as the optimal value.

3. Concentrations of Hydrogen Peroxide and NaOH

Figure 4:
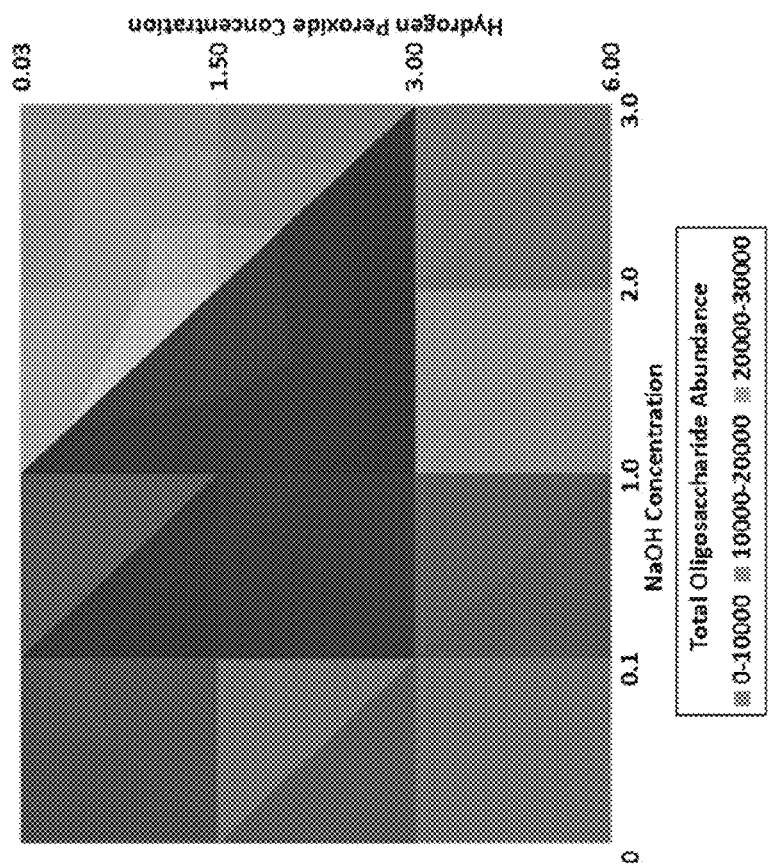
FIG. 4. Optimization of NaOH and Hydrogen Peroxide concentrations.

An important feature of this procedure is the use of the basic NaOH solution to terminate the reaction. This step is key to producing abundant oligosaccharide products. To optimize the condition a full factorial design was used by varying the NaOH concentration, the $H_2O_2$ concentration and the abundances of the oligosaccharides. The concentrations of NaOH were, 0, 0.1, 1.0, 2.0, and 3.0 M. The concentrations of $H_2O_2$ were 0.02, 0.12, 0.24, and 0.48 M of hydrogen peroxide. There were little or no detectible oligosaccharide in the reaction mixture when no NaOH was added (0.0 M, FIG. 4). Similarly, no detectible oligosaccharides were observed when the $H_2O_2$ concentration fell below 0.02 M. No detectible oligosaccharide signal was observed when no $H_2O_2$ was added to the solution (FIG. 4). Based on this study, we find that 2.0 M of NaOH and 0.12 M of $H_2O_2$ worked well.

4. Reaction Time and Temperature

Figure 5:
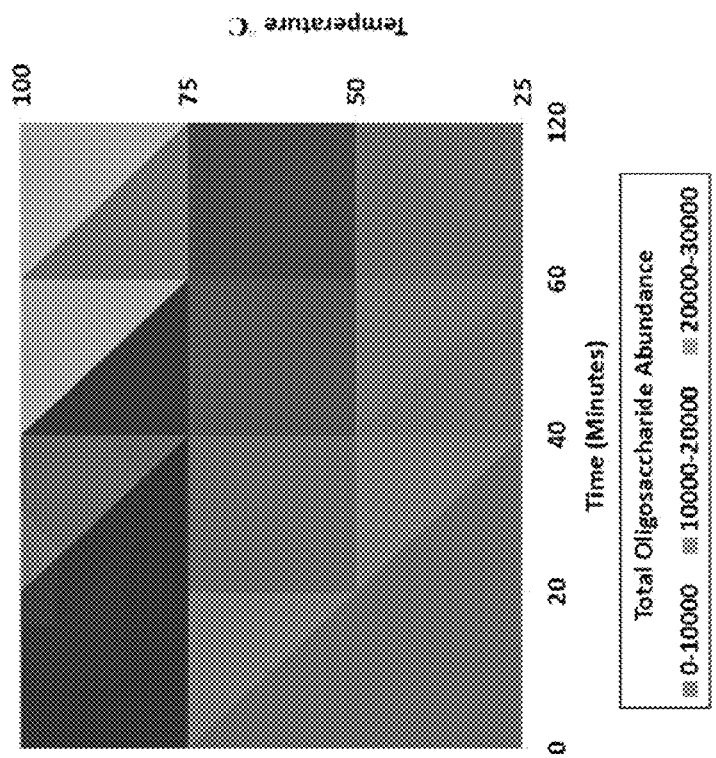
FIG. 5. Optimization of Time and Temperature conditions.

Time and temperature were analyzed also using a full factorial design. The time points of 0, 20, 40, 60, and 120 minutes were examined. Temperatures of 25, 50, 75, and 100° C. were used. Minimal oligosaccharide signals were observed below 75° C. The greatest abundances were observed at 100° C. and the reaction time of 20 minutes. (FIG. 5).

5. Effects of Other Transition Metals

Figure 6:
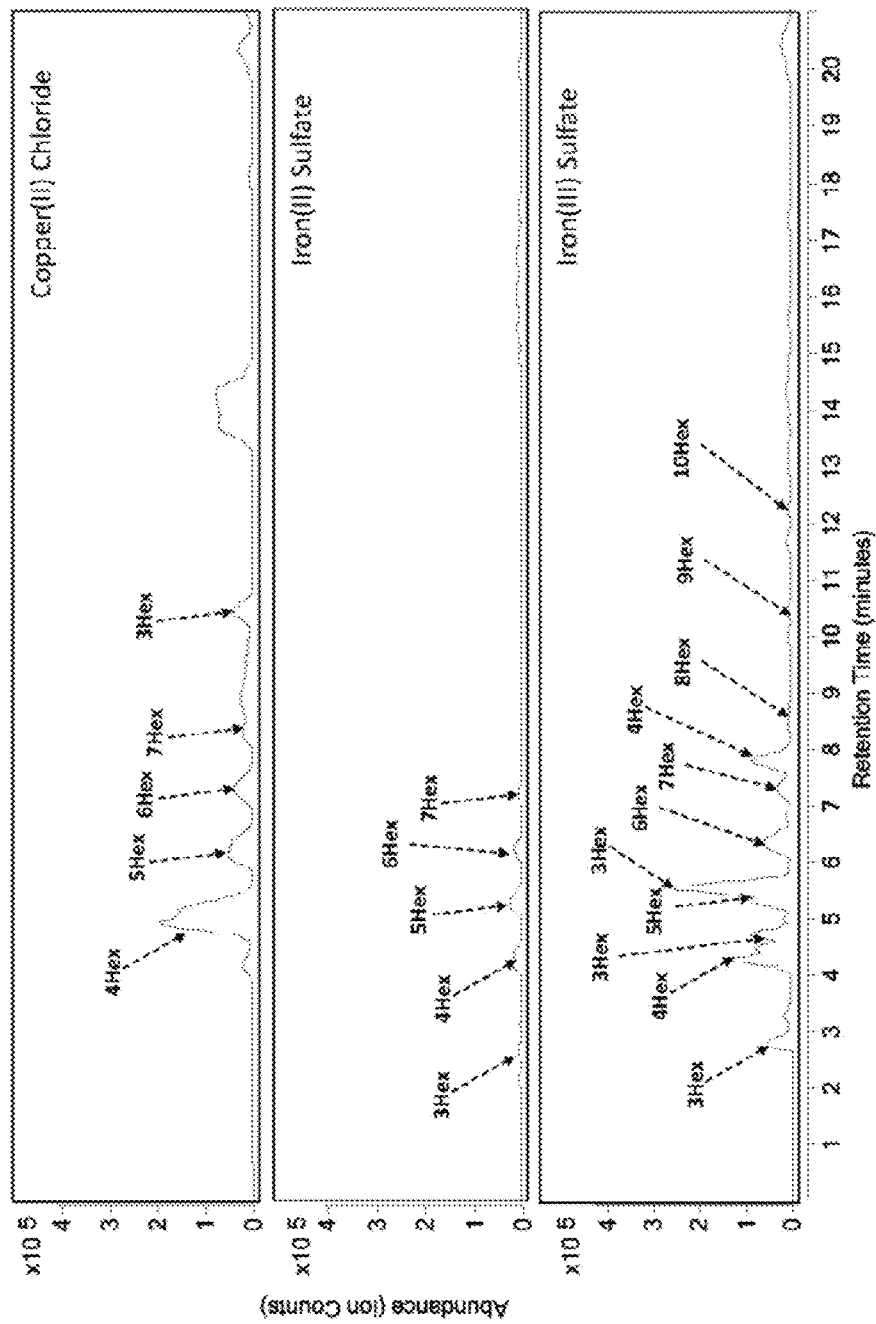
FIG. 6. HPLC-MS profile of oligosaccharides from green split pea generated by $CuCl_2$, $FeSO_4$, and $Fe_3(SO_4)_2$.

Fenton type reactions have shown to proceed with Fe(III) Fe(II) and Cu(II) containing compounds. Iron(III) sulfate, iron(II) sulfate, and copper(II) chloride were reacted with green split pea with the previously optimized conditions. All three transition metals generated oligosaccharides (FIG. 6). Copper(II) chloride produced oligosaccharides from 3 to 7 hexoses in length in high abundance, with Hex4 being the most abundant oligosaccharide. Iron(II) Sulfate also produced oligosaccharides from 3 to 7 hexoses in length, but 10-fold less abundant than in the copper(II) chloride sample. Iron(III) sulfate produced oligosaccharides from 3 to 10 hexoses in length, with equal or greater abundance than copper(II) chloride. This sample also generated several hexose isomers including three Hex3 isomers, and two Hex4 isomers. From this data, we found that different transition metals and oxidation states can generate oligosaccharides from polysaccharides. We also found that different transition metals can produce different oligosaccharide profiles, suggesting that each metal has differing specificity.

Application of Fenton's Reactions on Food Polysaccharide

Figure 7:
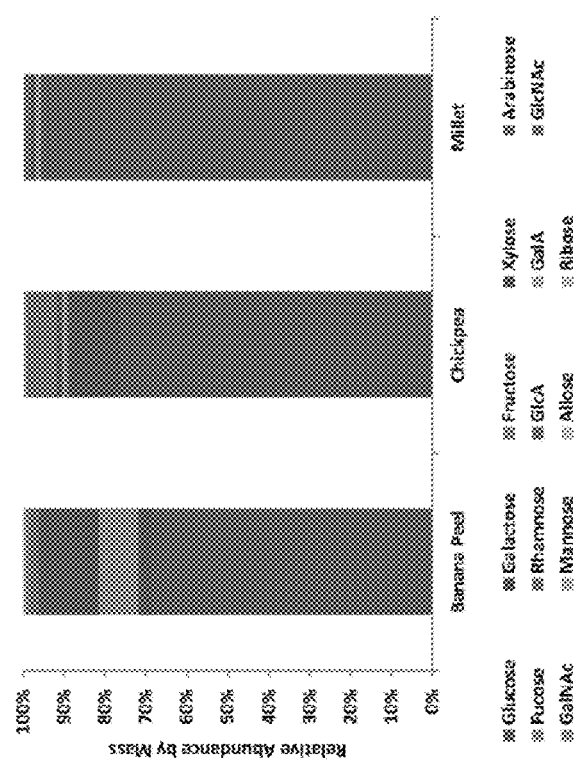
FIG. 7. Relative monosaccharide composition of foods that underwent FITDOG treatment.

Millet, chickpea, and banana peel were treated with FITDOG to show the types of oligosaccharides produced with different starting polysaccharides. Shown in FIG. 7 are the monosaccharide composition determined using the procedure described previously. Glucose is the most abundant component in all of the foods, however for the banana peel, there were greater abundances of xylose and fructose. For chickpea, there were greater abundances of arabinose and galactose. Millet contained primarily glucose (95.71%) (FIG. 7). This indicates that the hexose oligosaccharides that were liberated from FITDOG are of a glucose.

Figure 8:
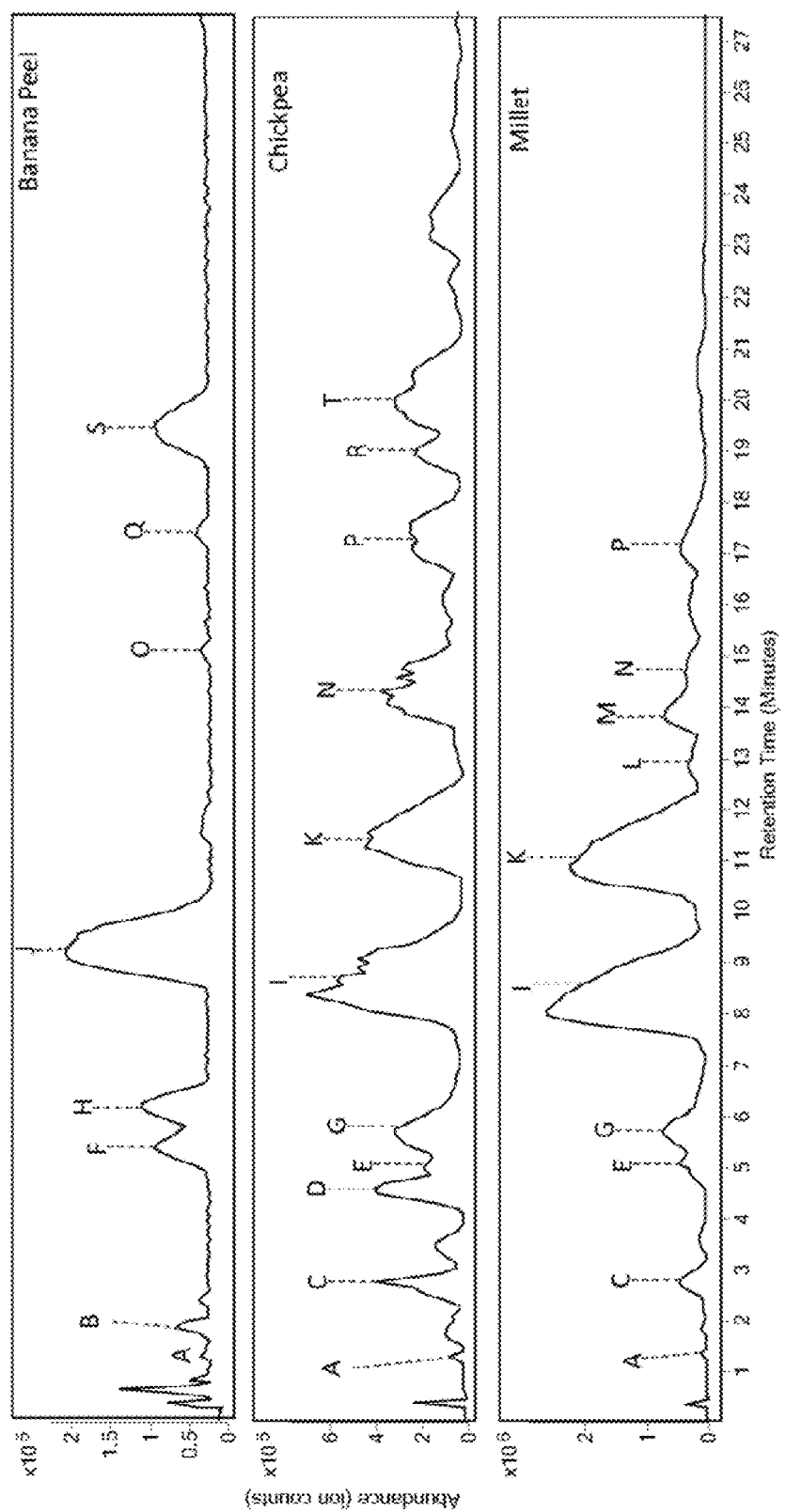
FIG. 8. Annotated base peak chromatograms for banana peel, chickpea, and millet that underwent FITDOG treatment. Annotations correspond with the compound designation in Table 1.

The liquid chromatography-mass spectrometry chromatogram summarizes the results for the three polysaccharides (FIG. 8). The peaks are listed with their oligosaccharide composition in Table 1. Each chromatogram yielded distinct peaks that differed according to their respective monosaccharide compositions.

Banana peel (upper panel) yielded primarily short oligomers including three isomers of the Hex3 (hexose trisaccharide A, B, and S). Hex or Hexose can be glucose or fructose, but likely glucose. The most abundant oligosaccharides correspond to Hex5 (J). Hex4 isomers are also observed (F and H). Chickpea was found to have a Hex2HexA1 species (D), HexA corresponds to hexuronic acid. Other abundant compounds Hex4 (C, E, G), Hex5 (I), Hex6 (K), and Hex7 (N and P) were observed. Millet (bottom panel) yielded Hex4 (C, E, and G) with low abundances of Hex3. Hex5 was present corresponding to the most abundance species I, while K corresponds to Hex6. Mixed combinations were observed as in L, which was composed of Hex5PentA1 and where PentA correspond to penturonic acid.

Prebiotic Activity of Oligosaccharides from Butternut Squash

Figure 9:
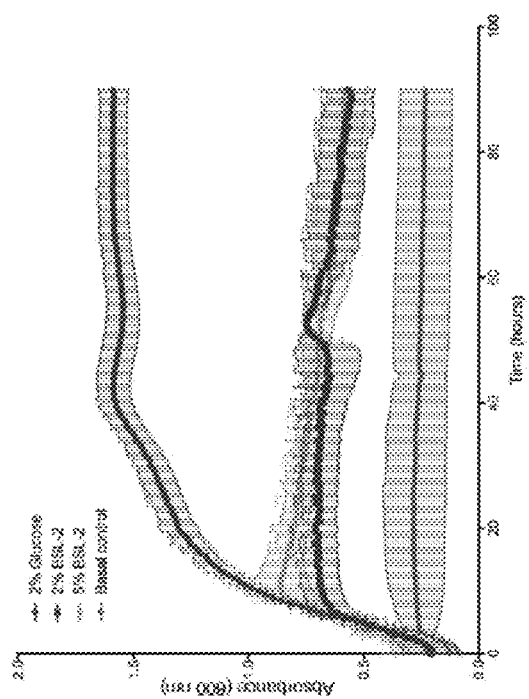
FIG. 9. The growth of *Bifidobacterium pseudocatenulatum* MP80 on oligosaccharides generated from the Fenton's oxidation of butternut squash.
Figure 10:
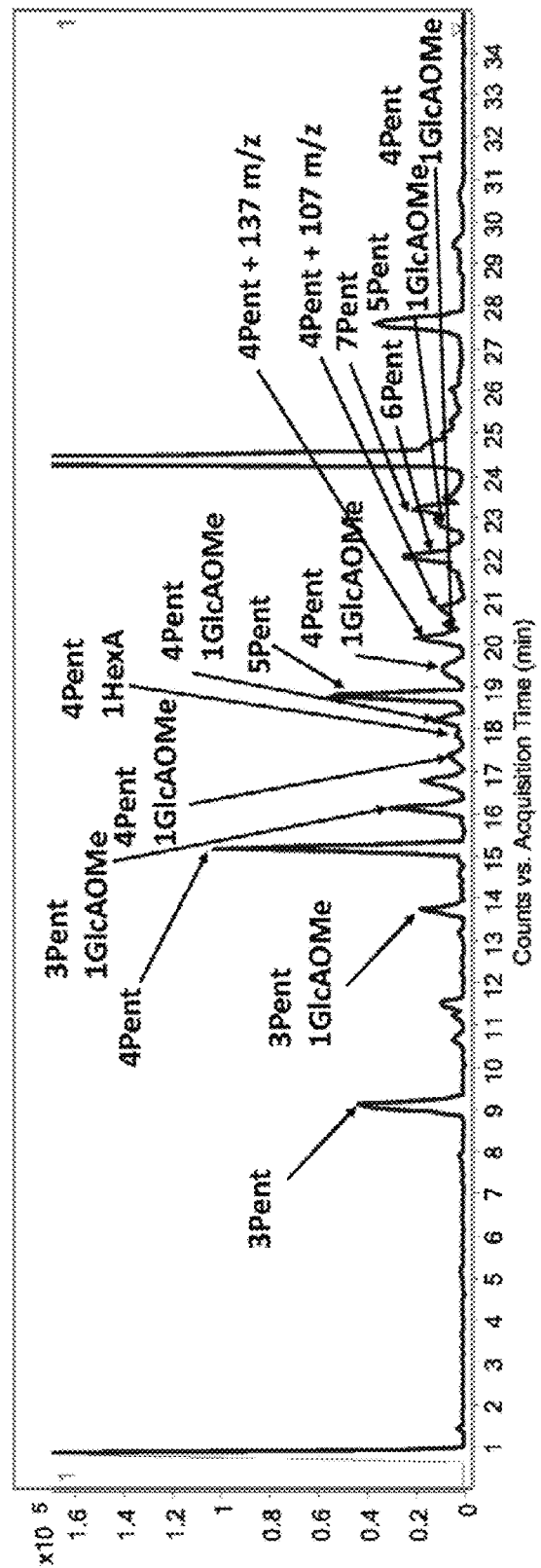
FIG. 10 shows annotated base peak chromatograms for xylan.
Figure 11:
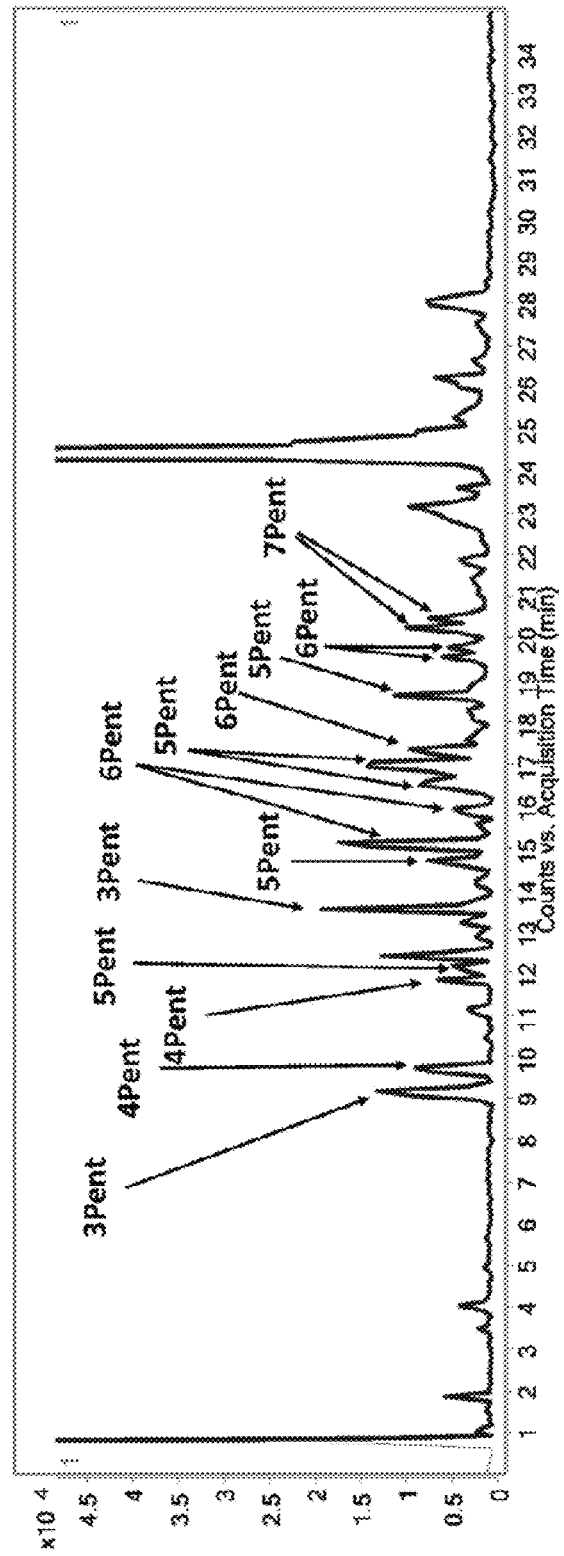
FIG. 11 shows annotated base peak chromatograms for arabinoxylan.
Figure 12:
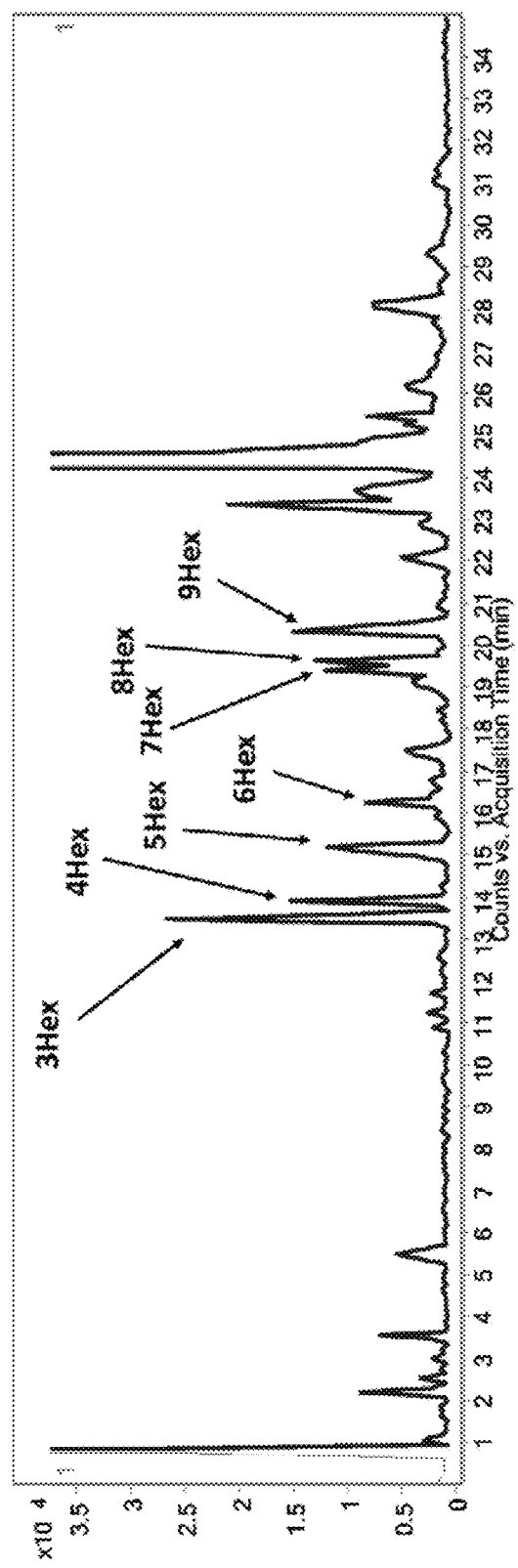
FIG. 12 shows annotated base peak chromatograms for lichenan.
Figure 13:
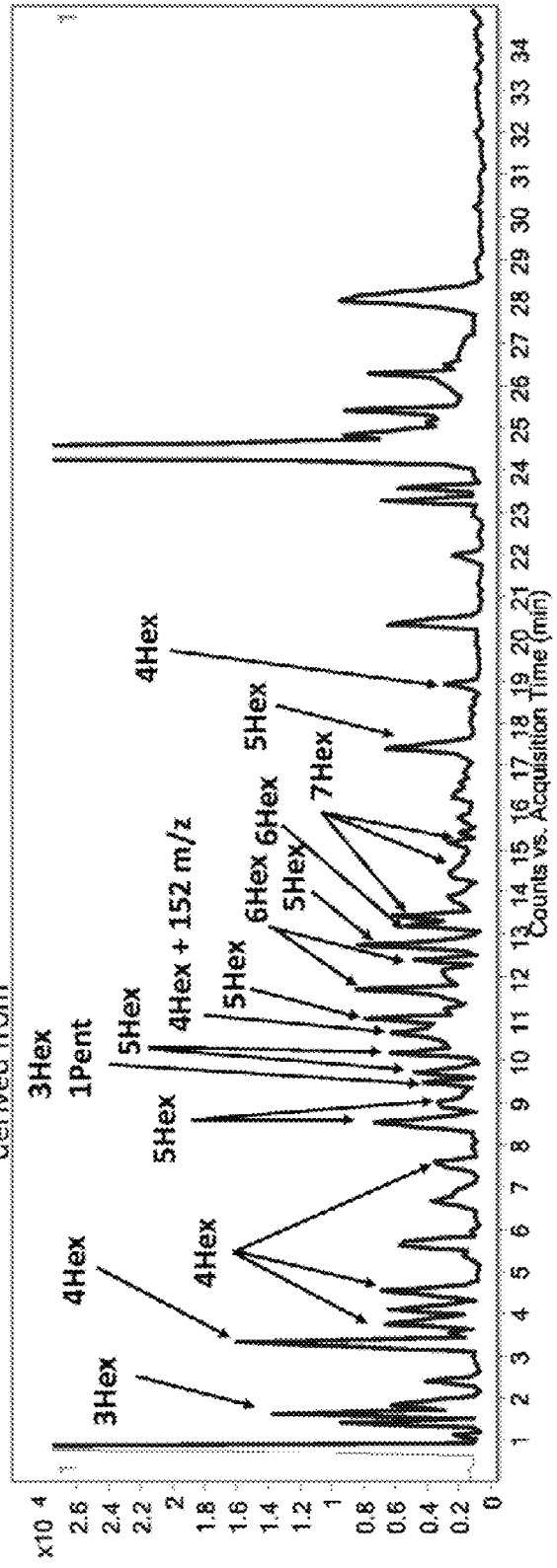
FIG. 13 shows annotated base peak chromatograms for galactomannan.
Figure 14:
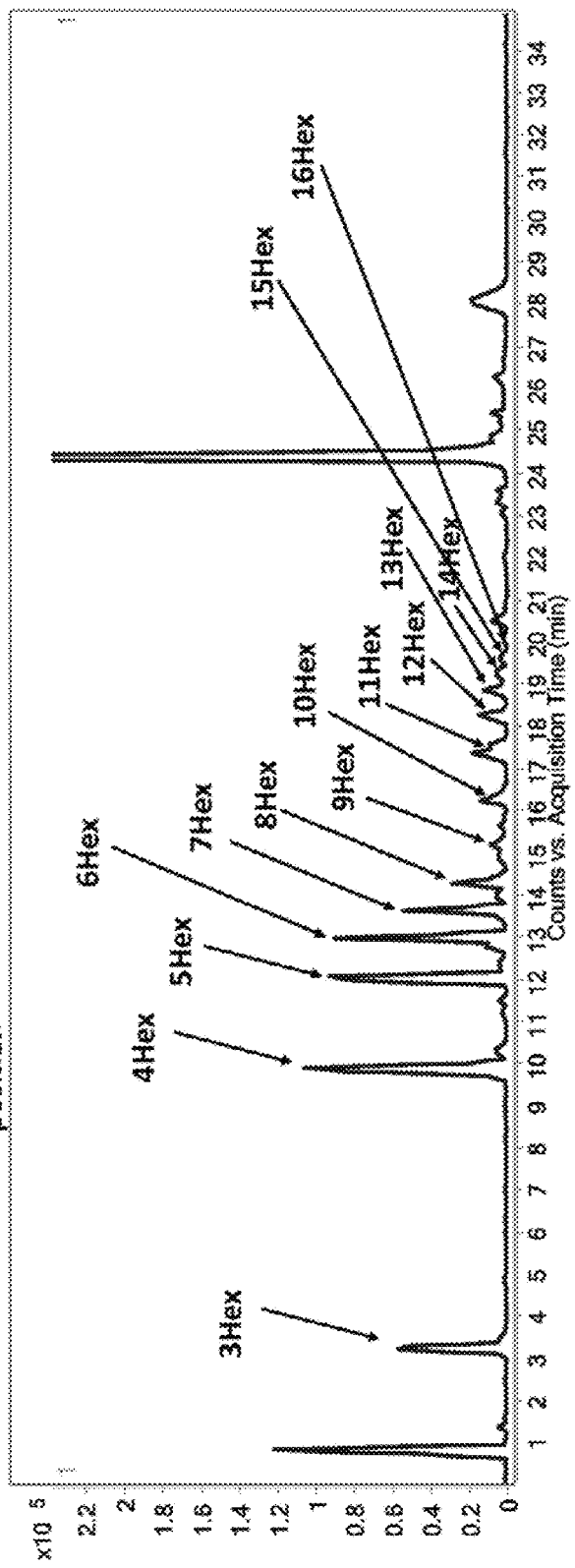
FIG. 14 shows annotated base peak chromatograms for amylopectin.
Figure 15:
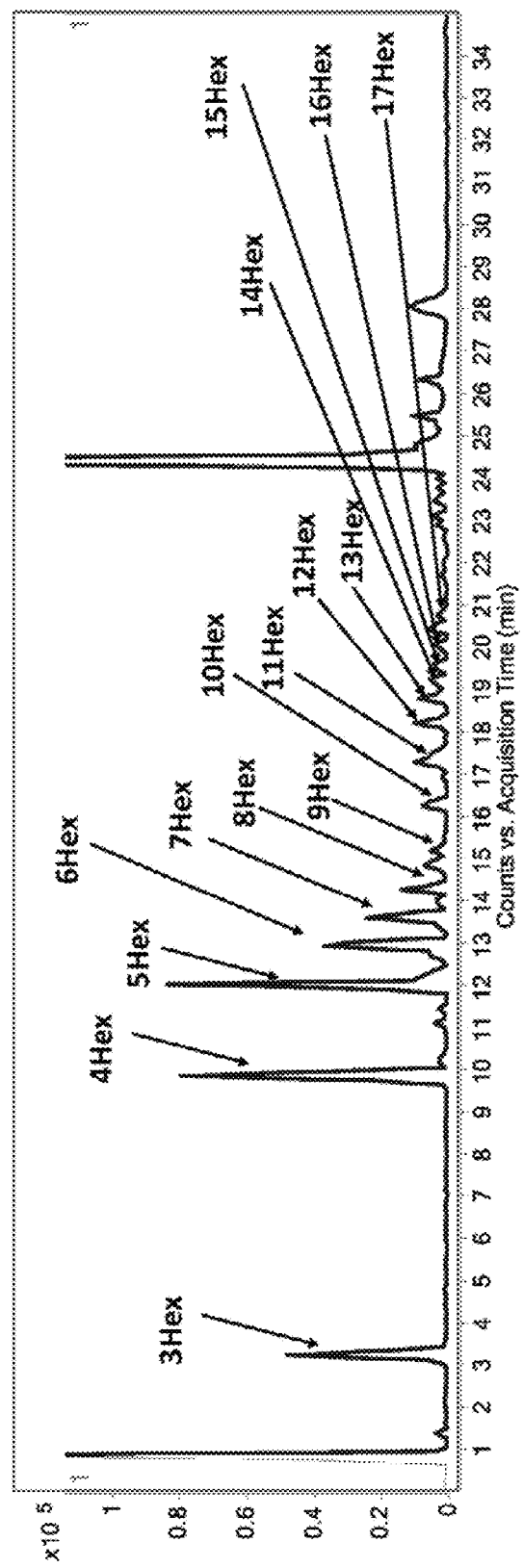
FIG. 15 shows annotated base peak chromatograms for amylose.
Figure 16:
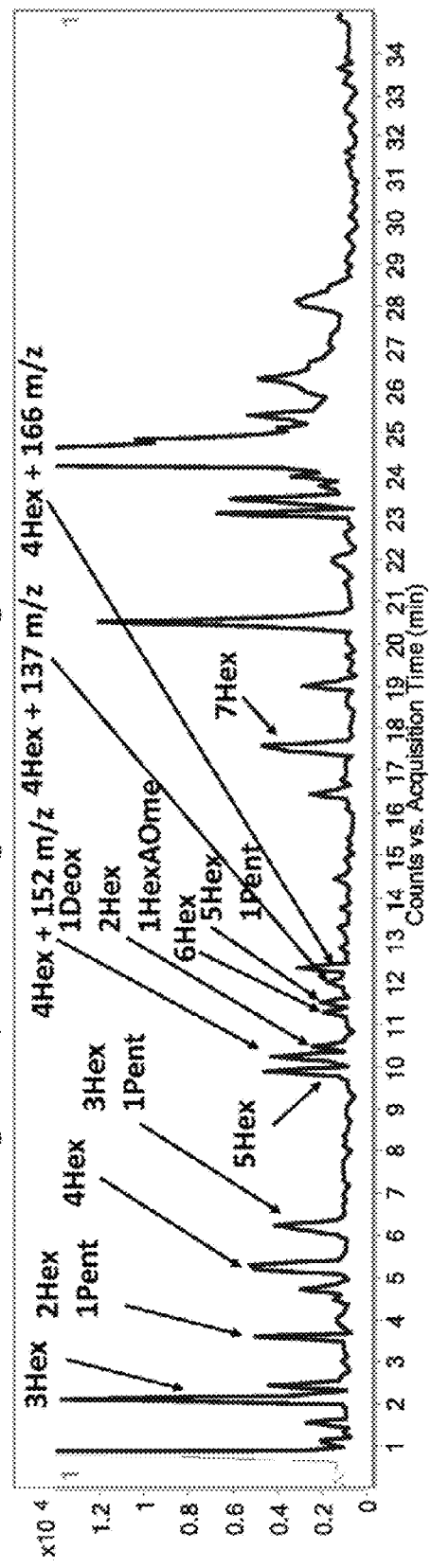
FIG. 16 shows annotated base peak chromatograms for rhamnogalacturonan I.
Figure 17:
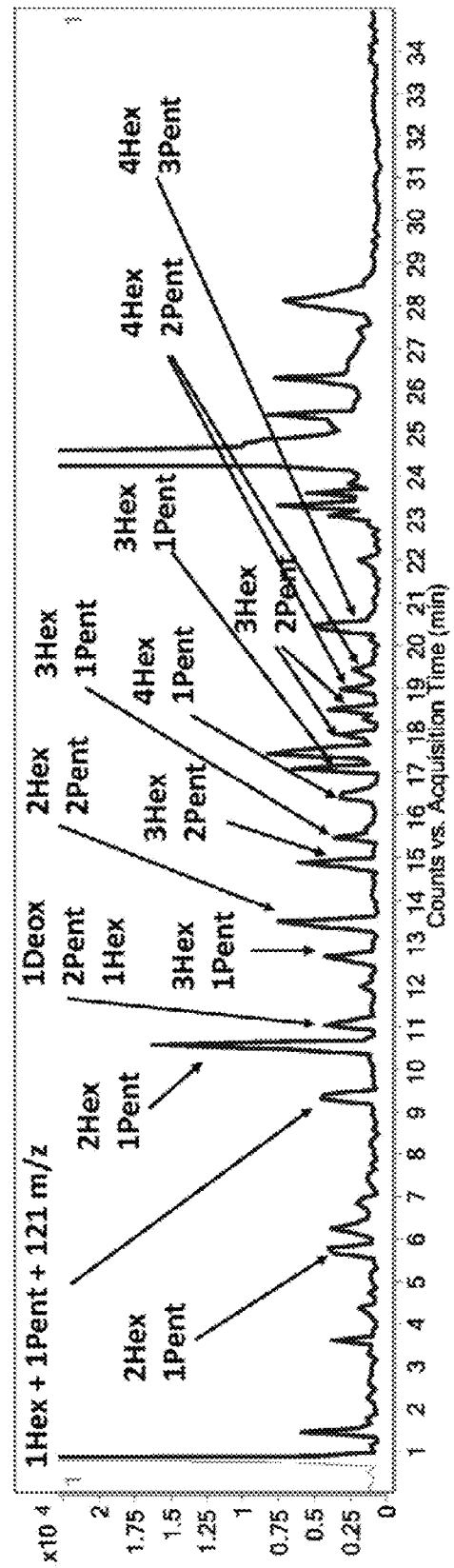
FIG. 17 shows annotated base peak chromatograms for xyloglucan.
Figure 18:
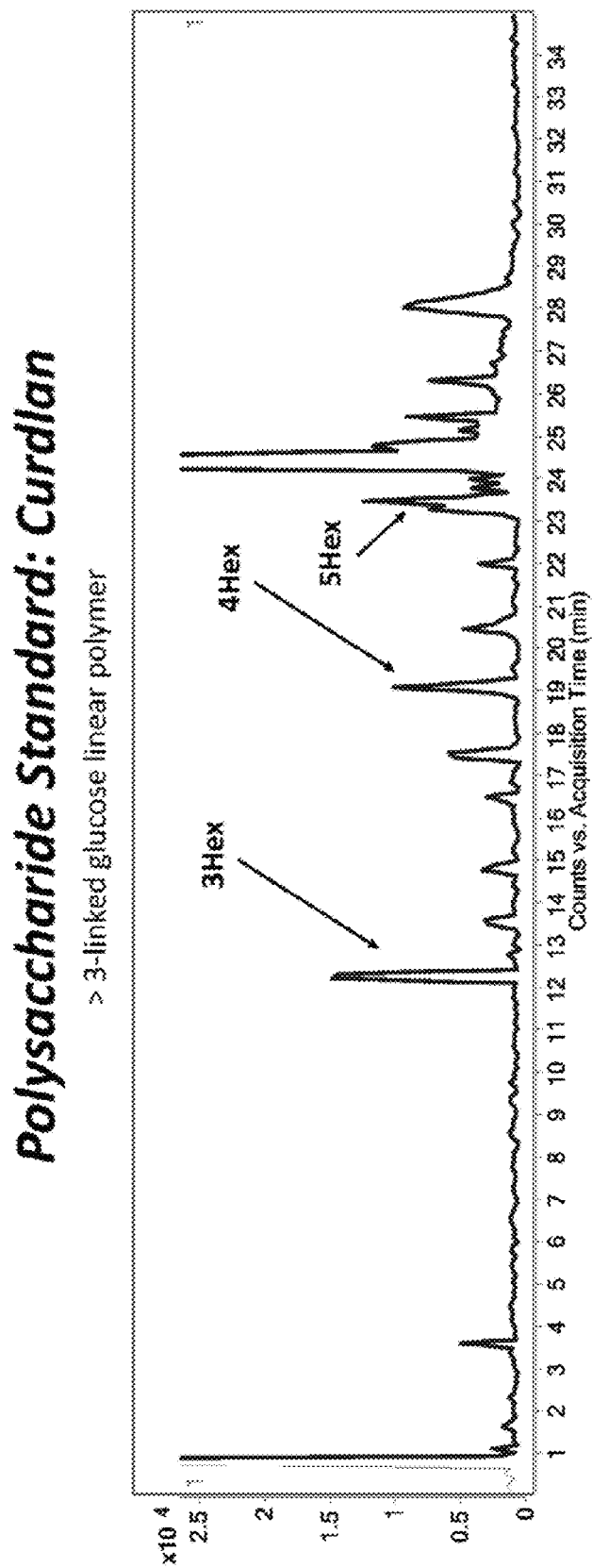
FIG. 18 shows annotated base peak chromatograms for curdlan.
Figure 19:
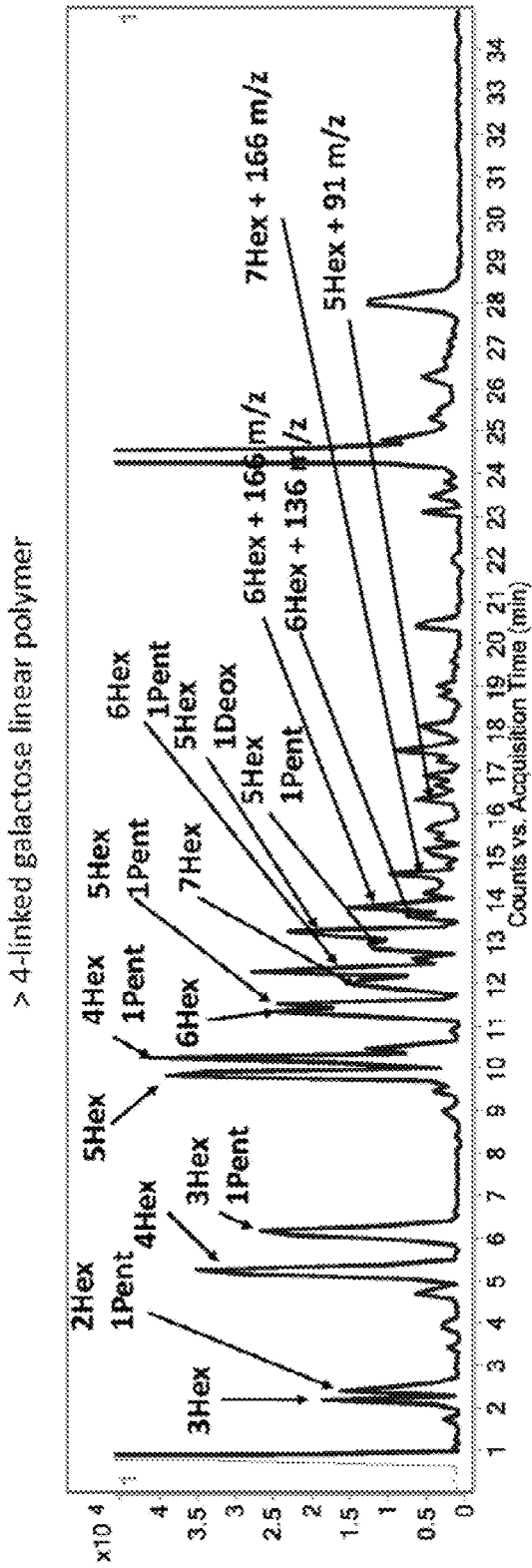
FIG. 19 shows annotated base peak chromatograms for galactan.
Figure 20:
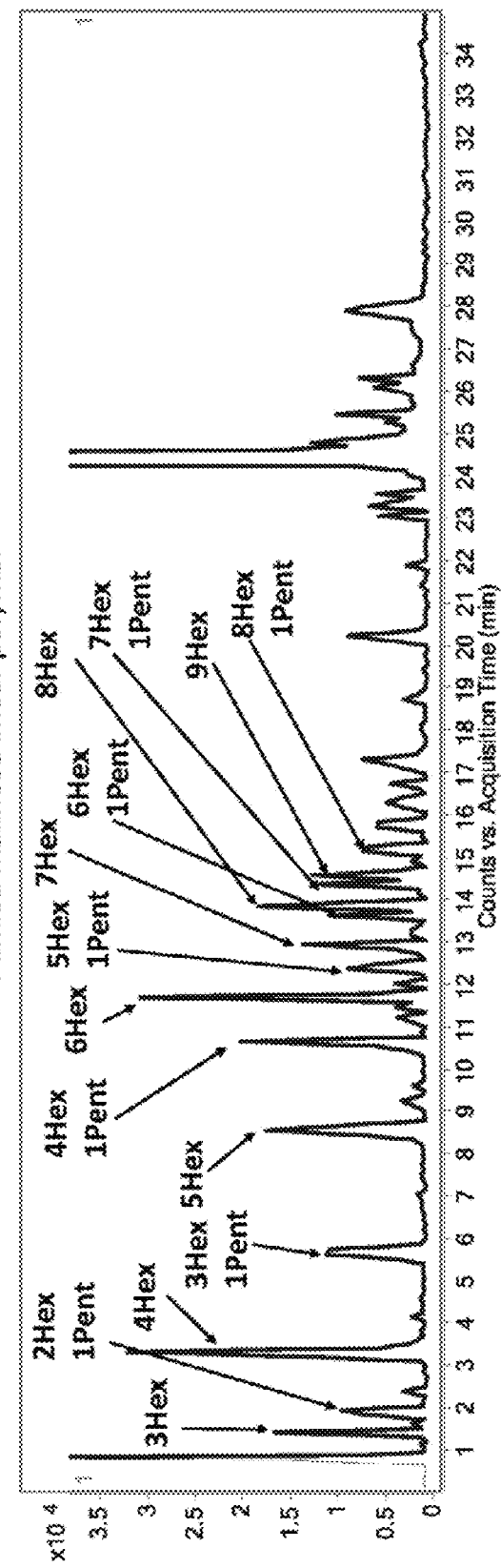
FIG. 20 shows annotated base peak chromatograms for mannan.
Figure 21:
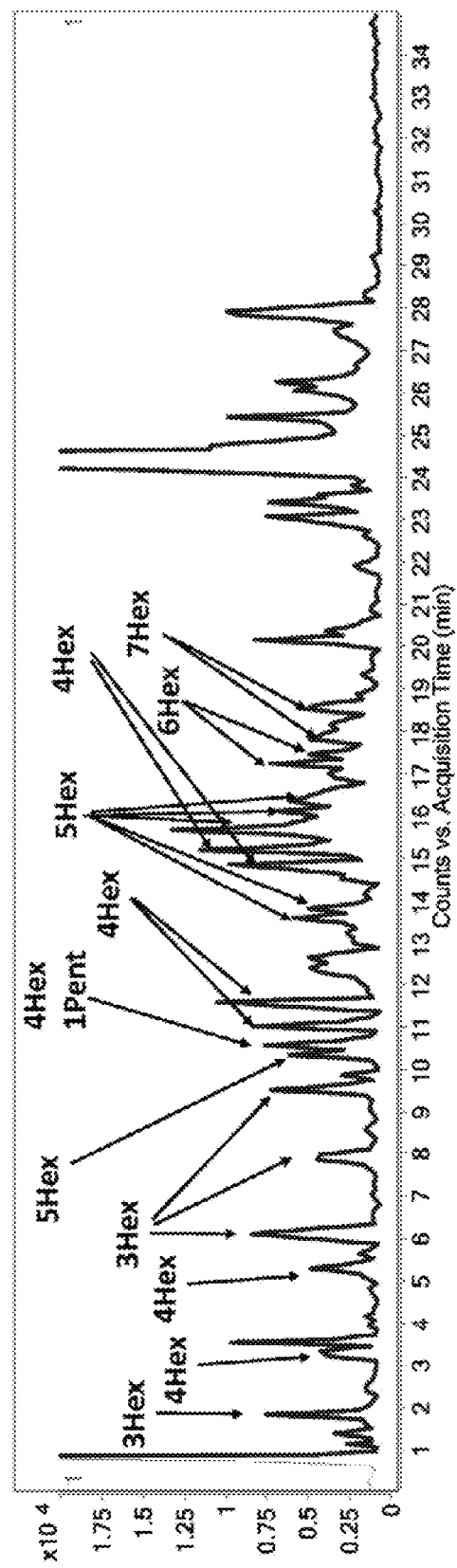
FIG. 21 shows annotated base peak chromatograms for glucomannan.
Figure 22:
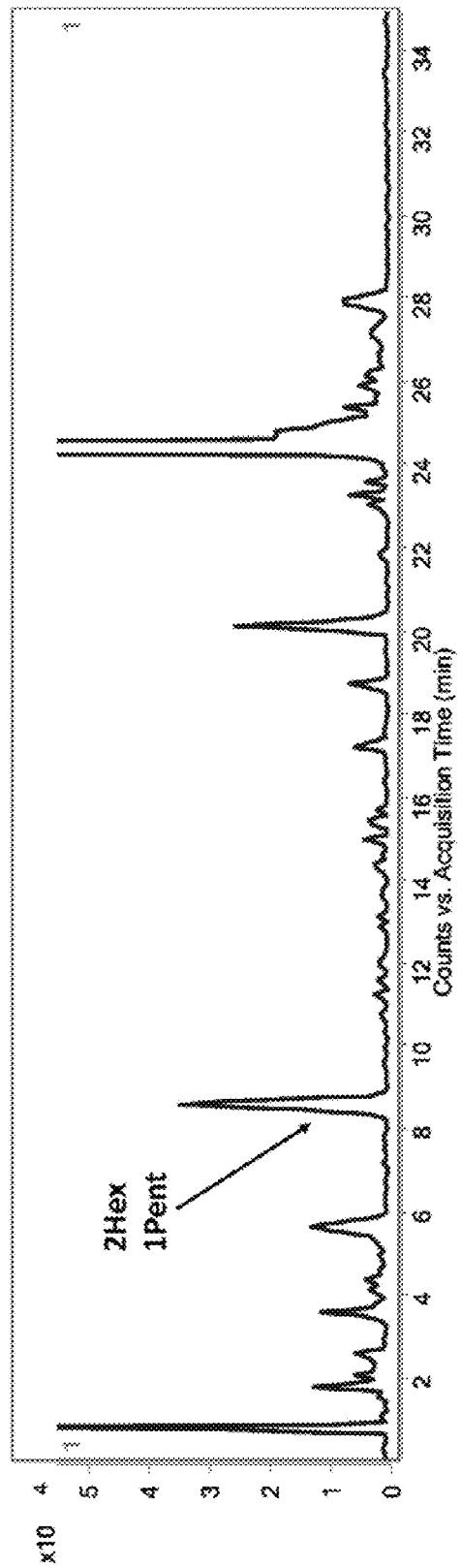
FIG. 22 shows annotated base peak chromatograms for larch arabinogalactan.
Figure 23:
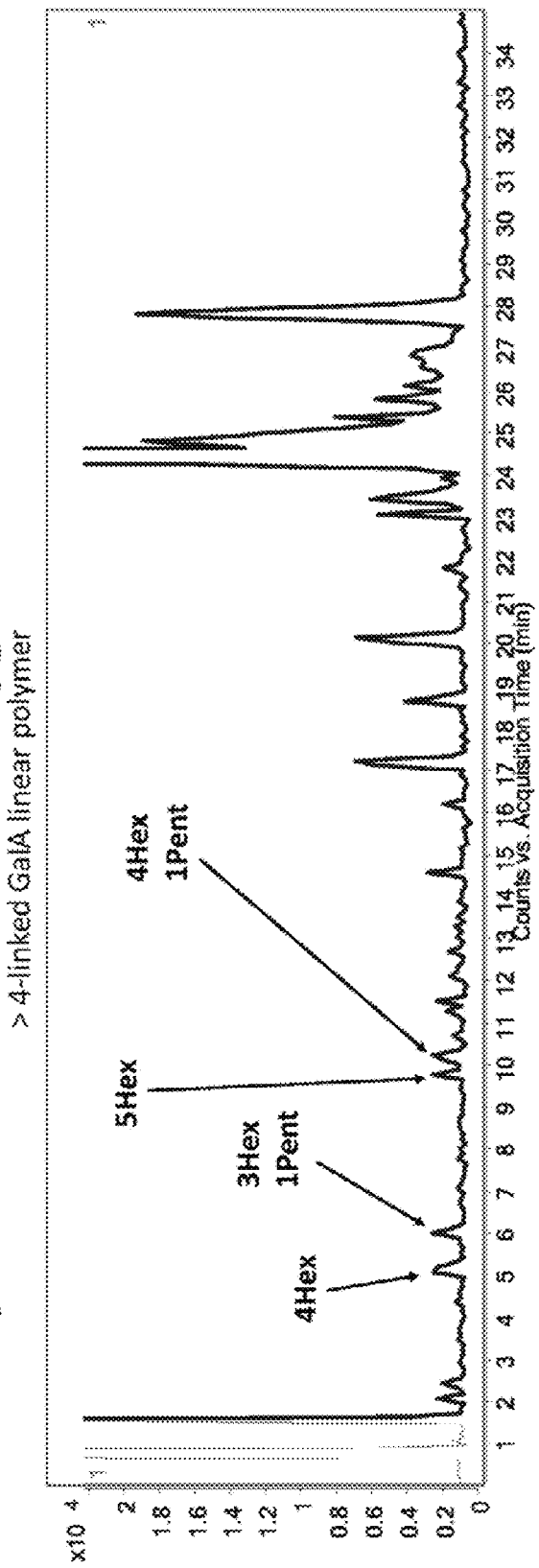
FIG. 23 shows annotated base peak chromatograms for polygalacturonic acid.
Figure 24:
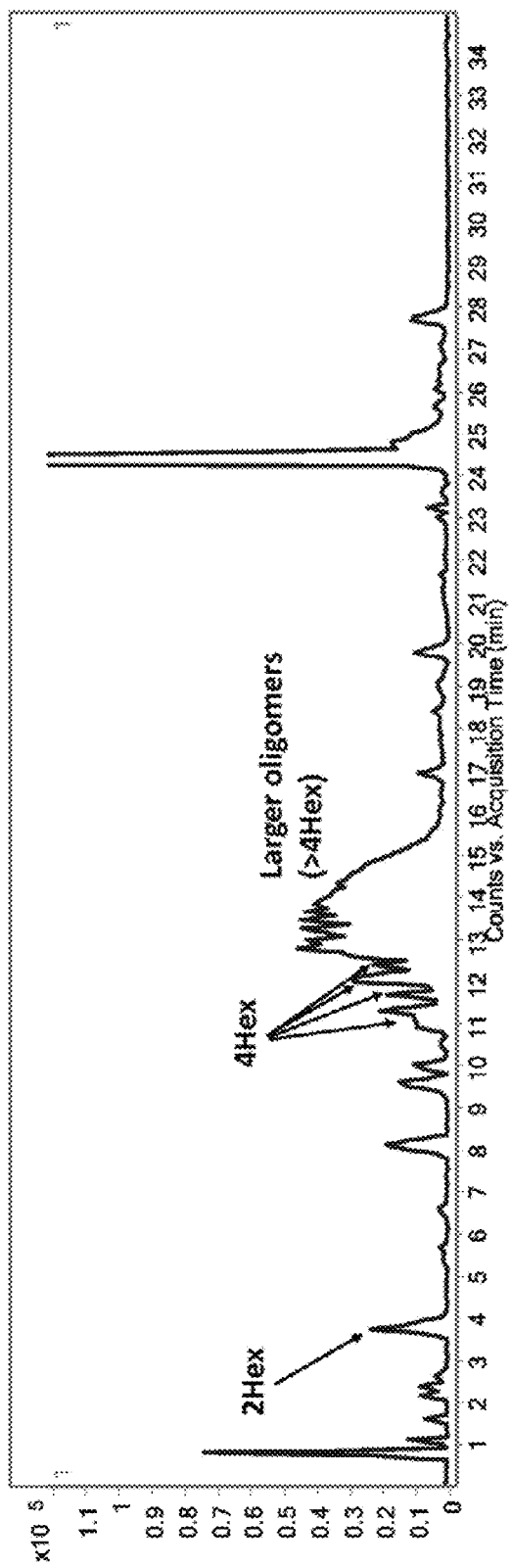
FIG. 24 shows annotated base peak chromatograms for inulin.

Several oligosaccharides from the FITDOG of various food polysaccharides were examined for their prebiotic activity. An example is provided using the oligosaccharides from butternut squash. The profile of the oligosaccharides were similar to those obtained above. In this example *B. Pseudocatenulatum* MP80 was grown on oligosaccharides generated from the Fenton's oxidation of butternut squash. In contrast to other strains tested, *B. pseudocatenulatum* MP80 was able to grow on both 2% and 5% solutions of butternut squash oligosaccharides. The growth ultimately reached a maximum OD of 0.962 in the 5% solution. Growth in butternut squash oligosaccharides was significantly higher than the negative control (max. OD of 0.378) but lower than the positive control (FIG. 9). As other tested strains did not grow on the butternut squash oligosaccharides, this result shows that these oligosaccharides selectively allow the growth of certain bacteria.

TABLE 1

Library of the most abundant compounds found from the FITDOG treatment on several foods.

| Compound Designation | Retention Time | m/z | Composition | Banana Peel | Chickpea | Millet |
|---|---|---|---|---|---|---|
| A | 1.89 | 505.17 | 3Hex | X | X | X |
| B | 2.3 | 505.17 | 3Hex | X | | |
| C | 2.8 | 667.26 | 4Hex | | X | X |
| D | 4.56 | 519.19 | 2Hex + 1HexA | | X | |
| E | 5.05 | 667.23 | 4Hex | | X | X |
| F | 5.47 | 667.23 | 4Hex | X | | |
| G | 5.76 | 667.23 | 4Hex | | X | X |
| H | 6.18 | 667.23 | 4Hex | X | | |
| I | 8.54 | 829.28 | 5Hex | | X | X |
| J | 9.46 | 829.28 | 5Hex | X | | |
| K | 11.32 | 991.34 | 6Hex | | X | X |
| L | 12.92 | 959.31 | 5Hex + (1Penturonic) | | | X |
| M | 13.83 | 887.29 | 5Hex + (76.02) | | | X |
| N | 14.39 | 1153.39 | 7Hex | | X | X |
| O | 15.12 | 887.29 | 5Hex + (76.02) | X | | |
| P | 17.11 | 1049.34 | 6Hex + (76.02) | | X | X |
| Q | 17.41 | 521.17 | 2Hex + (1HexA-2H) | X | | |
| R | 18.93 | 1301.43 | 7Hex + (1Penturonic) | | X | |
| S | 19.44 | 505.17 | 3Hex | X | | |
| T | 19.89 | 1211.39 | 7hex + (76.02) | | X | |

"X" represents which foods a compound was found.

Example 2

Figure 28:
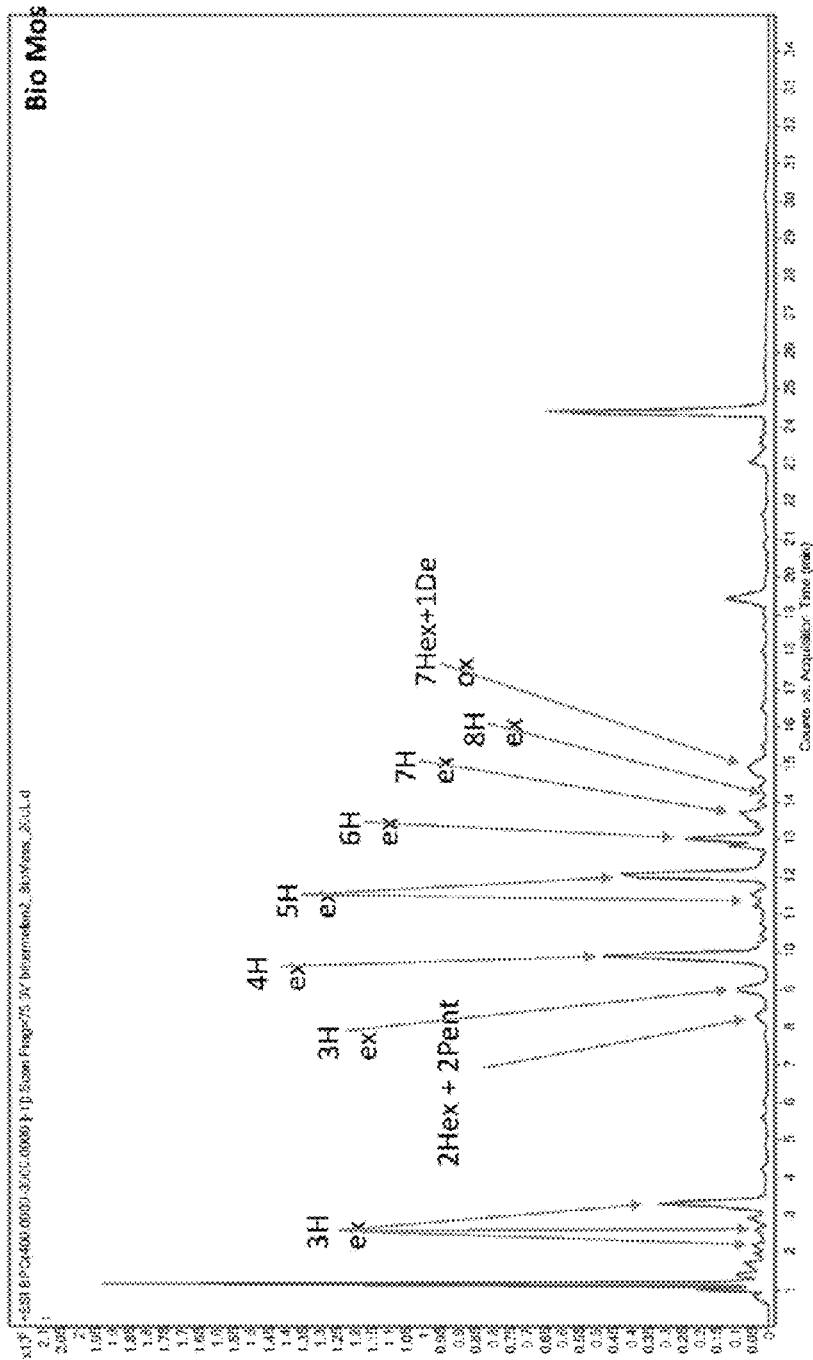
FIG. 28 shows annotated base peak chromatograms for yeast cell wall polysaccharide.
Figure 29:
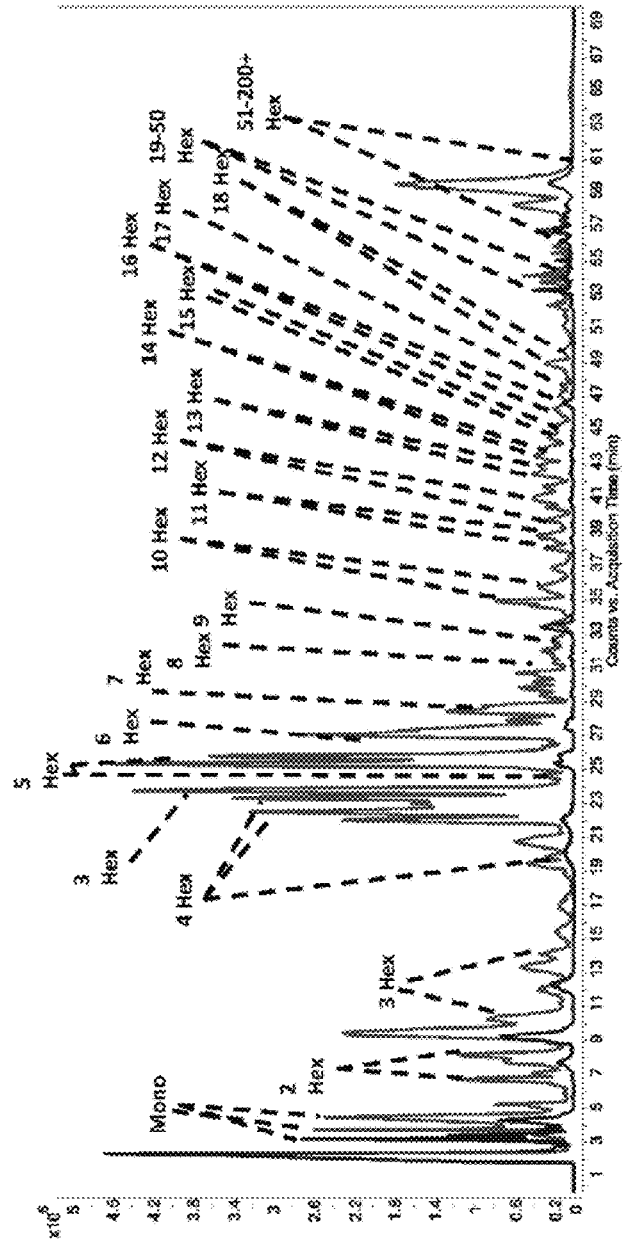
FIG. 29 shows annotated base peak chromatograms for butternut squash that underwent liter scale FITDOG, showing a range of polymerization from 1-200+ Hexoses. This data was analyzed on a nano-chip-HPLC/Q-TOF mass spectrometer. Degrees of polymerization from 4-7 Hexoses were shown to be in the greatest abundance.

The results below illustrate the utility of the Fitdog method on complicated mixtures of polysaccharides and pure polysaccharides. The complicated mixtures of polysaccharides include butternut squash (note that oligosaccharides from 3-200 are produced (FIG. 29)). The method can be used on yeast cell wall (FIG. 28). The method also works on purified polysaccharides including xylan, rye arabinoxylan, lichenan, galactomannan, amylopectin, amylose, rhamnogalacturonan I, xyloglucan, curdlan, galactan, mannan, glucomannan, larch arabionogalactan, polygalacturonic acid, inulin (FIGS. 10-24 and 27).

Figure 25:
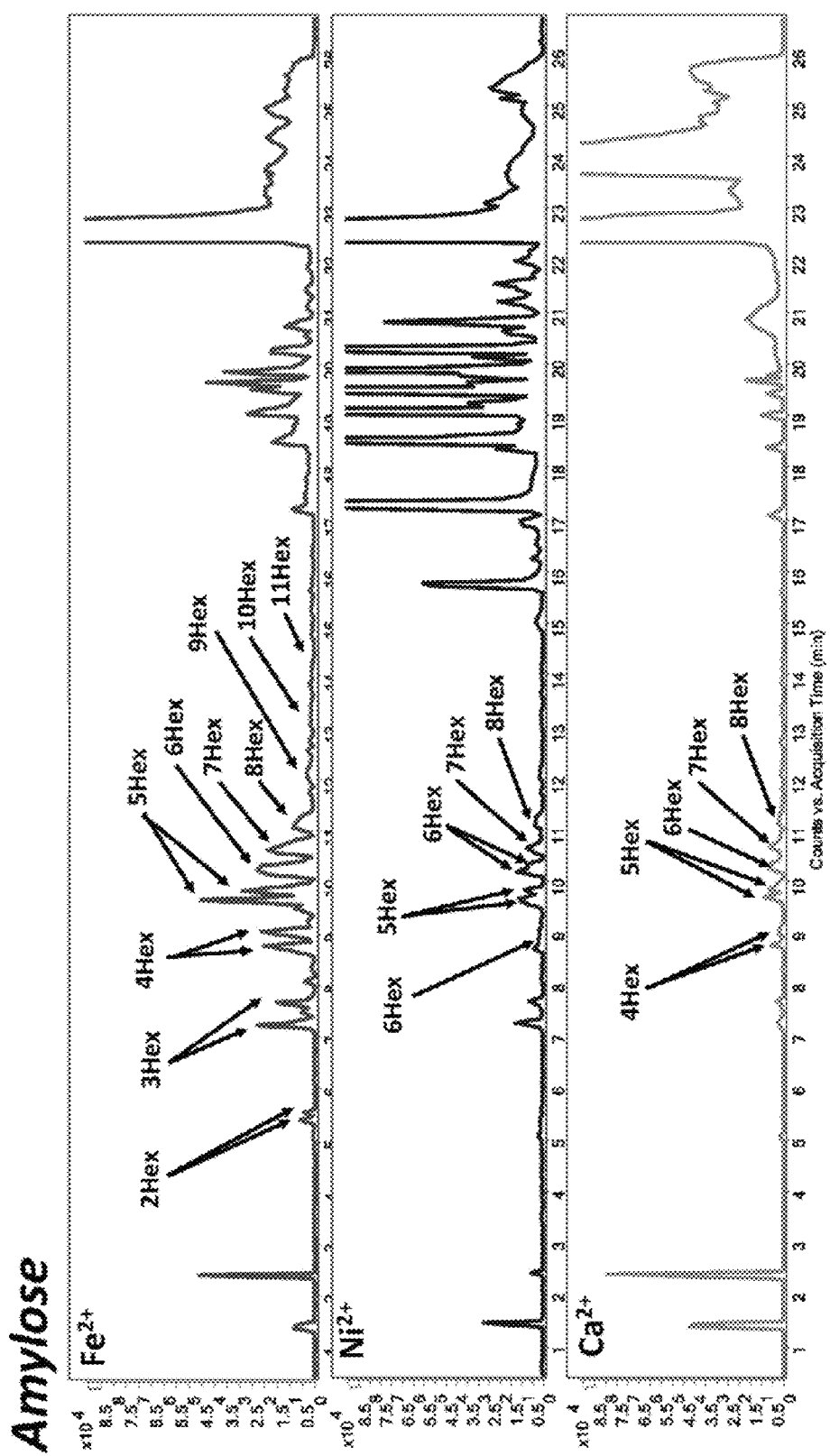
FIG. 25 shows annotated base peak chromatograms for amylose in which different metals were used in the Fitdog method.
Figure 26:
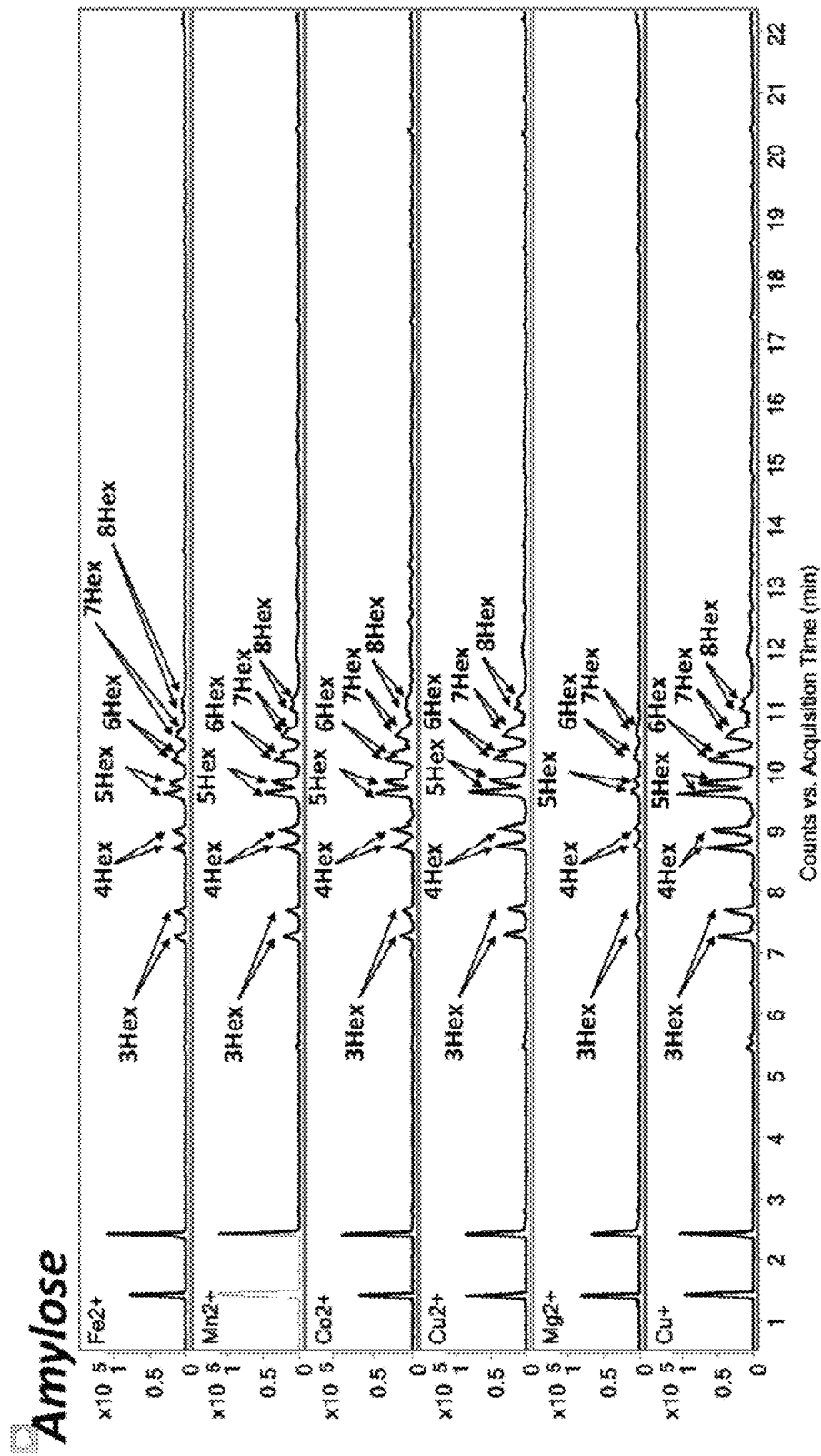
FIG. 26 shows annotated base peak chromatograms for amylose in which different metals were used in the Fitdog method.
Figure 27:
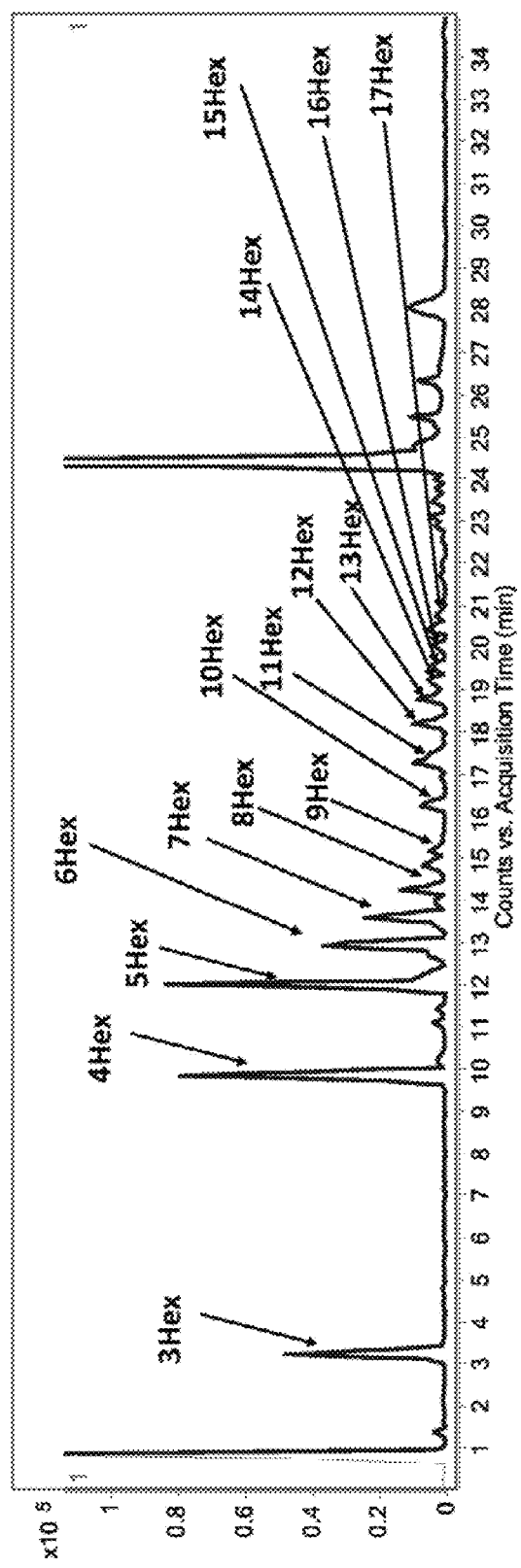
FIG. 27 shows annotated base peak chromatograms for amylose.

Different metals have been used for the FITDOG method. They include Fe, Ni, Ca, Cu, and Mg. They produce oligosaccharides with varying DP distribution (FIGS. 25-26).

Materials:

Xylan, Rye Arabinoxylan, Lichenan, Galactomannan, Amylose, Rhamnogalacturonan I, Xyloglucan, Curdlan, Galactan, Mannan, Glucomannan, Larch Arabinogalactan, Polygalacturonic Acid, and Inulin were purchased from Megazyme (UK). Amylopectin was purchased from Sigma-Aldrich (St. Louis, Mo.).

Sodium Acetate, hydrogen peroxide (30% w/w), sodium hydroxide, iron(III) sulfate pentahydrate, iron(II) sulfate heptahydrate, copper(II) sulfate heptahydrate, copper(I) chloride, manganese(II) sulfate, cobalt(II) sulfate heptahydrate, magnesium sulfate, calcium chloride, nickel(II) chloride, and glacial acetic acid were all purchased from Sigma-Aldrich (St. Louis, Mo.).

Methods:

Oligosaccharide Production

A solution was prepared containing 95% (v/v) sodium acetate buffer adjusted to pH 5 with glacial acetic acid, 5% (v/v) hydrogen peroxide (30% w/w), and 65 nM of the metal complex under investigation. This mixture was vortexed and was added to dry polysaccharide standards to make a final solution of 1 mg/ml. The reaction was incubated at 100° C. for 60 minutes. After reacting, half of the reaction volume of cold 2 M NaOH was added and vortexed before adding 0.6% of the initial reaction volume of glacial acetic acid to neutralize.

Oligosaccharide Purification

Oligosaccharides were isolated using nonporous graphitized carbon cartridges (GCC-SPE). Cartridges were washed with 80% acetonitrile in 0.1% (v/v) trifluoroacetic acid (TFA) and nano-pure water. The oligosaccharides were loaded and washed with 5 column volumes of nano-pure water. The oligosaccharides were eluted with 40% acetonitrile with 0.05% (v/v) TFA.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of generating oligosaccharides from polysaccharides, the method comprising,
reacting polysaccharides in a reaction mixture under suitable reaction conditions with hydrogen peroxide and a transition metal or an alkaline earth metal; followed by
quenching the reaction by adding a base and/or cleaving glycosidic linkages in the polysaccharides by adding a base, thereby generating a mixture of oligosaccharides from the polysaccharides.

2. The method of claim 1, wherein the reaction mixture comprises a transition metal.

3. The method of claim 2, wherein the transition metal is selected from iron, copper, manganese, cobalt, or molybdenum.

4. The method of claim 1, wherein the reaction mixture comprises an alkaline earth metal.

5. The method of claim 4, wherein the alkaline earth metal is selected from calcium or magnesium.

6. The method of claim 1, wherein the transition metal in the reaction mixture is at a concentration of at least 0.65 nM.

7. The method of claim 1, wherein the transition metal in the reaction mixture is at a concentration from 0.65 nM to 500 nM.

8. The method of claim 1, wherein the hydrogen peroxide in the reaction mixture is at a concentration of at least 0.02M.

9. The method of claim 1, wherein the hydrogen peroxide in the reaction mixture is at a concentration of from 0.02 M to 1M.

10. The method of claim 1, wherein the base is sodium hydroxide, potassium hydroxide or calcium hydroxide.

11. The method of claim 1, wherein the base is at a concentration of at least 0.1M.

12. The method of claim 1, wherein the base is at a concentration of from 0.1 M-5.0 M.

13. The method of claim 1, wherein the polysaccharides include one or more of amylase, amylopectin, betaglucan, pullulan, xyloglucan, arabinogalactan I and arbinogalactan II, rhamnogalacturonan I, rhamnogalacturonan II, galactan, arabinan, arabinoxylan, xylan, glycogen, mannan, glucomannan, curdlan, or inulin.

14. The method of claim 1, wherein the polysaccharides are in the form of plant material.

15. The method of claim 1, further comprising purifying one or more oligosaccharide from the mixture of oligosaccharides.

16. The method of claim 1, wherein prior to the reacting, the method comprises contacting polysaccharides with one or more polysaccharide degrading enzyme.

17. The method of claim 16, wherein the one or more polysaccharide degrading enzyme comprises an amylase, isoamylase, cellulase, maltase, glucanase, or a combination thereof.

18. The method of claim 1, wherein the step of reacting polysaccharides in a reaction mixture with hydrogen peroxide and a transition metal or an alkaline earth metal has a reaction time of 20 minutes or longer.

19. The method of claim 1, wherein the step of reacting polysaccharides in a reaction mixture with hydrogen peroxide and a transition metal or an alkaline earth metal has a reaction time between 20 minutes and 120 minutes.

20. The method of claim 3, wherein the transition metal is Fe(III).

21. The method of claim 3, wherein the transition metal is Fe(II).

22. The method of claim 3, wherein the transition metal is Cu(II).

23. The method of claim 3, wherein the transition metal is Cu(I).

24. The method of claim 20, wherein the Fe(III) is added to the reaction in the form of $Fe_2(SO_4)_3$ at a concentration between 0.65 nM and 65 nM.

* * * * *